United States Patent
Ikku et al.

(10) Patent No.: US 7,518,109 B2
(45) Date of Patent: Apr. 14, 2009

(54) METHOD AND APPARATUS OF MEASURING THIN FILM SAMPLE AND METHOD AND APPARATUS OF FABRICATING THIN FILM SAMPLE

(75) Inventors: Yutaka Ikku, Chiba (JP); Tatsuya Asahata, Chiba (JP); Hidekazu Suzuki, Chiba (JP)

(73) Assignee: SII NanoTechnology Inc., Chiba-shi (JP)

(*) Notice: Subject to any disclaimer, the term of this patent is extended or adjusted under 35 U.S.C. 154(b) by 101 days.

(21) Appl. No.: 11/824,994

(22) Filed: Jul. 2, 2007

(65) Prior Publication Data

US 2008/0067384 A1    Mar. 20, 2008

Related U.S. Application Data

(63) Continuation of application No. PCT/JP2005/023566, filed on Dec. 22, 2005.

(30) Foreign Application Priority Data

Jan. 7, 2005    (JP)    ............................... 2005-002710

(51) Int. Cl.
G01N 23/225    (2006.01)
(52) U.S. Cl. .................. 250/310; 250/306; 250/307; 250/311; 702/172
(58) Field of Classification Search ............... 250/306, 250/307, 309, 310, 311; 702/155, 170, 172
See application file for complete search history.

(56) References Cited

U.S. PATENT DOCUMENTS

| | | | |
|---|---|---|---|
| H589 H * | 2/1989 | Sartore | ............ 250/307 |
| 5,656,811 A | 8/1997 | Itoh et al. | |
| 2003/0132381 A1* | 7/2003 | Itagaki et al. | ............ 250/310 |
| 2006/0157341 A1 | 7/2006 | Fujii | |

FOREIGN PATENT DOCUMENTS

| | | |
|---|---|---|
| JP | 63-9807 A | 1/1988 |
| JP | 8-5528 A | 1/1996 |
| JP | 8-240518 A | 9/1996 |

OTHER PUBLICATIONS

International Preliminary Report issued Jul. 10, 2007 in PCT/JP2005/023566.

* cited by examiner

*Primary Examiner*—Jack I Berman
*Assistant Examiner*—Michael Maskell
(74) *Attorney, Agent, or Firm*—Brinks Hofer Gilson & Lione

(57) ABSTRACT

In a method of measuring a thin film sample of irradiating an electron beam to a thin film sample, detecting a generated secondary electron and measuring a film thickness of the thin film sample by utilizing the secondary electron, it is provided that the film thickness is measured accurately, in a short period of time and easily even when a current amount of the irradiated electron beam is varied. An electron beam 2b is irradiated, and a generated secondary electron 4 is detected by a secondary electron detector 6. A calculated value constituted by an amount of a secondary electron detected at a film thickness measuring region and an amount of a secondary electron detected at a reference region is calculated by first calculating means 11. A film thickness of the film thickness measuring region can be calculated from a calibration data of a standard thin film sample and the calculated value calculated by a sample 5.

20 Claims, 15 Drawing Sheets

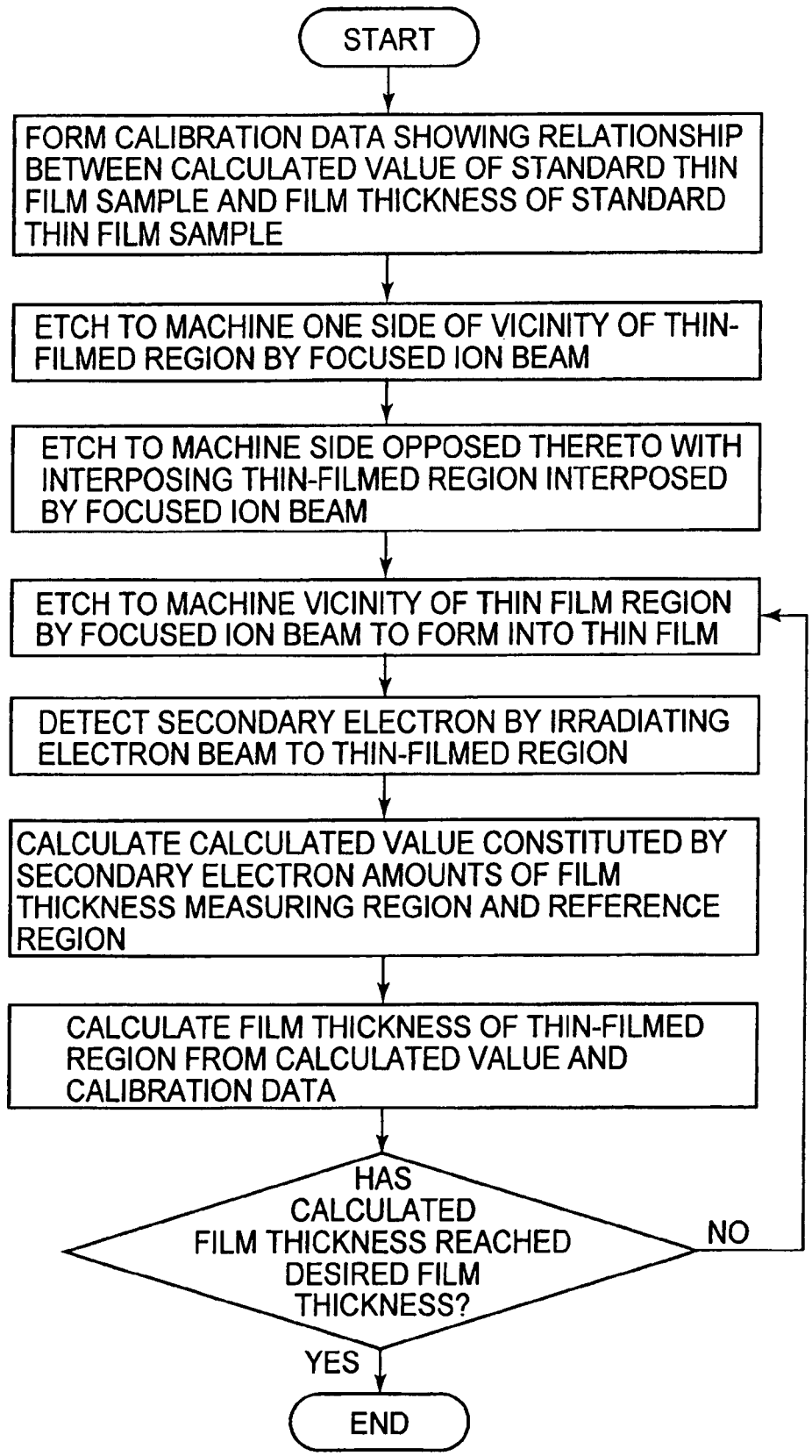

METHOD AND APPARATUS OF MEASURING THIN FILM SAMPLE AND METHOD AND APPARATUS OF FABRICATING THIN FILM SAMPLE

This application is a continuation of PCT/JP2005/023566, filed Dec. 22, 2005, which claims priority to Japanese Application No. JP2005-002710 filed Jan. 7, 2005. The entire contents of these applications are incorporated herein by reference.

BACKGROUND OF THE INVENTION

1. Technical Field

The present invention relates to a method and an apparatus of measuring a film thickness for measuring a film thickness of a thin film sample by using a charged particle beam as well as a method and an apparatus of fabricating a thin film sample for fabricating a thin film sample by using a focused ion beam.

2. Background Art

When a transmission electron microscope (TEM) or a scanning transmission electron microscope (STEM) is used for analyzing a specific portion of a semiconductor device or the like, the main stream is constituted by fabrication of a sample using a focused ion beam machining. In TEM or STEM observation, an image formed by irradiating an electron beam to a thin film sample having a thickness to a degree of capable of transmitting electrons and enlarging a transmitted electron beam is acquired and observed. In order to acquire a clear observation image by the method, it is important to accurately measure a film thickness of a sample machined into a thin film by a focused ion beam.

Further, various micromachining technologies have been developed in accordance with a miniaturization of a semiconductor process in recent years. Not only fabrication of a sample for TEM or STEM but also a technology of accurately measuring a film thickness of a thin sample as in a thin film is requested in fabricating a microstructure.

As a background art method of measuring a thickness of a thin film in forming a sample into a thin film by irradiating an ion beam, there is disclosed a method of irradiating an electron beam to a sample face of the thin film and monitoring a thickness of a thin film from a secondary electron detecting amount detected by a secondary electron detector (refer to, for example, JP-A-8-240518).

An explanation will be given as follows by using a sectional view of a sample showing a method of measuring a film thickness of a background art of FIG. 20. Numeral 28 designates a region of diverging incident electrons at inside of an observation region 27, numeral 6 designates secondary electrons generated from the observation region 27, numeral 8 designates a secondary electron detector for detecting the secondary electron 6, and the secondary electron detector 8 is connected with a monitor apparatus for quantitatively monitoring a film thickness of the observation region 27 from an intensity of the secondary electron 6. When the observation region 27 is formed by irradiating a focused ion beam 21b, an electron beam 2b is irradiated to the observation region 27. Although when the electron beam 2b is irradiated thereto, the secondary electrons 4 are generated, in a case in which the film thickness of the observation region 27 is thick, the secondary electrons 4 are not generated from a face opposed to an incident face. However, in accordance with forming the observation region 27 into a thin film by etching machining by the focused ion beam 21b, an amount of secondary electrons generated from a side opposed to a side of being irradiated with the electron beam is increased. Therefore, the film thickness of the observation region 27 is quantitatively monitored from an amount of detecting the secondary electrons by the secondary electron detector 8 and an end point of focused ion beam machining can be determined.

According to the method and the apparatus of measuring a film thickness for quantitatively monitoring the film thickness from the secondary electron detecting amount of the background art mentioned above, it is necessary to acquire a calibration data by previously using a standard thin film sample to establish a relationship between the film thickness of the thin film and the secondary electron amount. At that occasion, the secondary electron amount is changed by a current amount of an incident electron beam, and therefore, the beam current amount of the electron beam needs to stay the same when the calibration data is acquired by using a standard thin film sample and when a film thickness of a desired sample is measured.

However, the current amount of the electron beam is changed over time in view of a property of an electron source, and a variation in the current amount is unavoidable even when the current amount is controlled by an electron optical system. Therefore, according to the method and the apparatus of measuring the film thickness, there is a case in which the current amount of the electron beam irradiated to the thin film is varied and the electron beam current amount when the calibration data is acquired by using the standard sample and the electron beam current amount when the film thickness of the desired sample is measured differ from each other, and therefore, the film thickness cannot be measured accurately. Further, when the film thickness of the desired sample is measured, the current amount of the electron beam can be adjusted to be the same as that when the calibration data is acquired by using the standard thin film sample by adjusting the electron optical system by measuring the current amount of the electron beam. However, according to the method, there poses a problem that time is taken, particularly when film thicknesses of a plurality of samples are measured, the film thicknesses cannot be measured easily in a short period of time.

The invention intends to resolve the problem provided to the method and the apparatus of the background art and it is an object thereof to measure a film thickness accurately, in a short period of time, and easily even when a current amount of a charged particle beam of an electron beam or the like to be irradiated is varied.

SUMMARY OF THE INVENTION

Further, the invention provides following means in order to achieve the above-described object.

A method of measuring a thin film sample of the invention is characterized in including a step of detecting a charged particle beam generated by irradiating a charged particle to a region including a film thickness measuring region and a reference region of a standard thin film sample, a step of calculating a calculated value of the standard thin film sample constituted by an amount of the charged particle detected at the film thickness measuring region and an amount of the charged particle detected at the reference region, a step of forming a calibration data showing a relationship between the calculated value and the film thickness of the standard thin film sample, a step of detecting a charged particle generated by irradiating a charged particle beam to a region including a film thickness measuring region and a reference region of a desired thin film sample, a step of calculating a calculated value of the thin film sample constituted by an amount of the charged particle detected at the film thickness measuring region and an amount of the charged particle detected at the reference region, and a step of calculating the film thickness of the film thickness measuring region of the thin film sample from the calibration data and the calculated value of the thin film sample. Here, the standard thin film sample constitutes a portion having a material the same as that of a desired thin film sample and having a kind of a device the same as that of the desired thin film sample and is a sample a film thickness of which is known. Further, the reference region is a region at inside of a portion of the thin film sample through which the charged particle beam does not transmit.

Further, second problem resolving means uses a method of measuring a thin film sample characterized in including a step of detecting a charged particle generated by irradiating a charged particle beam to a region including a film thickness measuring region and a reference region of a standard thin film sample, a step of displaying an image of the charged particle on a display member by converting the detected charged particle into a luminance signal, a step of designating the film thickness measuring region and the reference region from the displayed image of the charged particle, a step of calculating a calculated value of the standard thin film sample constituted by a luminance of the film thickness measuring region and a luminance of the reference region, a step of forming a calibration data showing a relationship between the calculated value and the film thickness of the standard thin film sample, a step of detecting a charged particle generated by irradiating a charged particle beam to a region including a film thickness measuring region and a reference region of a desired thin film sample, a step of displaying an image of the charged particle on a display member by converting a detected charged particle into a luminance signal, a step of designating the film thickness measuring region and the reference region from a displayed image of the charged particle, a step of calculating a calculated value of the thin film sample constituted by a luminance of the film thickness measuring region and a luminance of the reference region, and a step of calculating the film thickness of the film thickness measuring region of the thin film sample from the calibration data and the calculated value of the thin film sample. Here, the luminance is constituted by converting a signal of the charged particle into a brightness displayed on the display member in order to display on the display member.

Further, third problem resolving means uses the method of measuring a thin film sample described in the first problem resolving means characterized in that the calculated values of the standard thin film sample and the thin film sample constituted by the amount of the charged particle detected at the film thickness measuring region and the amount of the charged particle detected at the reference region is a ratio of the amount of the charged particle detected at the film thickness measuring region to the amount of the charged particle detected at the reference region.

Further, fourth problem resolving means uses the method of measuring a thin film sample described in the second problem resolving means characterized in that the calculated value of the standard thin film sample and the thin film sample constituted by the luminance of the thin film measuring region and the luminance of the reference region is a ratio of the luminance of the film thickness measuring region to the luminance of the reference region.

Further, fifth problem resolving means is the method of measuring a thin film sample described in any one of the first through the fourth problem resolving means and uses the method of measuring a thin film sample characterized in that the calculated value of the thin film sample is calculated by using an average value of the amounts of the secondary charged particles at inside of the film thickness measuring region and an average value of the amounts of the secondary charged particles at inside of the reference region, or an average value of the luminances at the film thickness measuring region and an average value of the luminances at the reference region.

Further, sixth problem resolving means is the method of measuring a thin film sample described in any one of the first through the fourth problem resolving means and uses the method of measuring a thin film sample characterized in that an average value is calculated from the amounts of the charged particles or the luminances of a plurality of the reference regions and the calculated value of the thin film sample is calculated by using the average value.

Further, seventh problem resolving means is the method of measuring a thin film sample described in any one of the first through the fourth problem resolving means and uses the method of measuring a thin film sample characterized in that an average value is calculated from the amounts of the charged particles or the luminances of a plurality of the film thickness measuring regions and the calculated value of the thin film sample is calculated by using the average value.

Further, eighth problem resolving means is the method of measuring a thin film sample described in any one of the first through the fourth problem resolving means and uses the method of measuring a thin film sample characterized in that the film thicknesses of a plurality of the film thickness measuring regions are calculated.

Further, ninth problem resolving means is the method of measuring a thin film sample described in any one of the first through the fourth problem resolving means and uses the method of measuring a thin film sample characterized in that inside of the film thickness measuring region and inside of the reference region are constituted by a single material.

Further, tenth problem resolving means uses the method of measuring a thin film sample described in any one of the first through the ninth problem resolving means characterized in that a charged particle generated by irradiating the charged particle beam is constituted by a secondary electron.

Further, eleventh problem resolving means uses the method of measuring a thin film sample described in any one of the first through the ninth problem resolving means characterized in that a charged particle generated by irradiating the charged particle beam is constituted by a reflected electron.

Further, twelfth problem resolving means uses the method of measuring a thin film sample described in any one of the first through the ninth problem resolving means characterized in that a charged particle generated by irradiating the charged particle beam is added with a secondary electron and a reflected electron.

Further, thirteenth problem resolving means uses a method of fabricating a thin film sample characterized in including a step of scanning to irradiate a focused ion beam to a one side sample surface at a vicinity of a thin-filmed region of a desired sample to etch, a step of scanning to irradiate a focused ion beam to an opposed side sample surface to the one side sample surface by interposing the thin-filmed region to etch, a step of forming the thin-filmed region into a thin film by scanning to irradiate the focused ion beam to the vicinity of the thin-filmed region to etch, a step of calculating a film thickness of the thin-filmed region to form into thin film by the method of measuring a thin film sample according to any one of Claims 1 through 12, and a step of etching the thin-filmed region until the calculated film thickness reaches a desired film thickness to form into the thin film.

Further, fourteenth problem resolving means uses a method of fabricating a thin film sample characterized in including a step of forming a calibration data showing a relationship between an amount of irradiating a focused ion beam and a film thickness of etching a standard thin film sample by scanning to irradiate the focused ion beam to a surface of the standard thin film sample to etch, a step of scanning to irradiate a focused ion beam to a one side sample surface at a vicinity of a thin-filmed region of a desired sample to etch, a step of scanning to irradiate a focused ion beam to a sample surface on a side opposed to the one side sample surface by interposing the thin-filmed region to etch, a step of forming the thin-filmed region into a thin film by scanning to irradiate the focused ion beam to a vicinity of the thin-filmed region to etch, a step of calculating a film thickness of the thin-filmed region to form into thin film by the method of measuring a thin film sample according to any one of Claims 1 through 12, a step of calculating an amount of irradiating the focused ion beam necessary for making the calculated film thickness reach a desired film thickness from the calibration data, and a step of forming the thin-filmed region into the thin film by etching the thin-filmed region by the focused ion beam of the calculated irradiating amount.

Further, fifteenth problem resolving means uses an apparatus of measuring a thin film sample characterized in comprising a charged particle generating source for generating a charged particle, a charged particle optical system for slenderly narrowing the charged particle into a charged particle beam to irradiate a surface of a sample while scanning the charged particle beam, a charged particle detector for detecting a charged particle generated by irradiating the charged particle beam, a display member for displaying an image of the charged particle by converting the charged particle detected by the charged particle detector into a luminance signal, first calculating means for calculating a calculated value constituted by amounts of the charged particles or luminances of a plurality of regions, and second calculating means for calculating a film thickness of the film thickness measuring region from a calibration data constituting a function of a calculated value from a standard thin film sample constituted by amounts of the charged particles or luminances of a plurality of regions of the standard thin film sample and a film thickness of the standard thin film sample and the calculated value calculated by the first calculating means.

Further, sixteenth problem resolving means uses the apparatus of measuring a thin film sample described in the fifteenth problem resolving means characterized in that a charged particle generated by irradiating the charged particle beam is constituted by a secondary electron.

Further, seventeenth problem resolving means uses the apparatus of measuring a thin film sample described in the fifteenth problem resolving means characterized in that the charged particle generated by irradiating the charged particle beam is constituted by a reflected electron.

Further, eighteenth problem resolving means uses the apparatus of measuring a thin film sample described in the fifteenth problem resolving means characterized in that the charged particle generated by irradiating the charged particle beam is added with a secondary electron and the reflected electron.

Further, nineteenth problem resolving means uses an apparatus of fabricating a thin film sample characterized in that the apparatus of measuring a thin film sample further comprises an ion generating source for generating an ion, and an ion optical system for constituting an ion beam by slenderly narrowing the ion to irradiate a surface of a sample while scanning the ion beam for the apparatus of measuring a thin film sample described in any one of the fifteenth through the eighteenth problem resolving means.

Further, twentieth problem resolving means uses the apparatus of fabricating a thin film sample characterized in further comprising a third calculating mechanism for calculating an amount of irradiating the focused ion beam necessary for the film thickness calculated by the second calculating means to reach a desired film thickness for the apparatus of fabricating a thin film sample described in the nineteenth problem resolving means.

Operation by the first problem resolving means is as follows. By calculating the calculated value constituted by the amount of the charged particle detected at the film thickness measuring region and the amount of the charged particle detected at the reference region, even when a current amount of an electron beam to be irradiated is varied, the calculated value which is not effected with an influence thereof can be calculated. Here, the calculated value of the amount of the charged particle detected at the film thickness measuring region and the amount of the charged particle detected at the reference region is a function of an amount of a charged particle generated by the charged particle beam having the same beam current amount. That is, the function is a function uniquely determined by the film thickness at the film thickness measuring region without depending on the current amount of the charged particle beam to be irradiated. Therefore, even when beam current amounts of the charged particle beams irradiated to the thin film sample and the standard sample differ from each other, so far as the film thickness stays the same, the calculated value stays the same value. Therefore, even when the current amount of the charged particle beam to be irradiated is varied, the calculated value is not influenced thereby. Further, by calculating the film thickness of the film thickness measuring region from the calculated value and the calibration data, even when the current amount of the charged particle beam to be irradiated is varied, the film thickness of the film thickness measuring region can be acquired without being influenced thereby.

Operation by the second problem resolving means is as follows. The charged particle is converted into the luminance signal to display the image of the charged particle on the display member, by designating the film thickness measuring region and the reference region from the displayed image of the charged particle and calculating the calculated value constituted by the luminance of the film thickness measuring region and the luminance of the reference region, with regard to the film thickness measuring region designated from the image of the charged particle displayed on the display member, even when the current amount of the charged particle beam to be irradiated is varied, the film thickness of the film thickness measuring region can be acquired without being influenced thereby.

Operation by the fifth problem resolving means is as follows. In calculating the calculated value, by calculating the calculated value by using the average value of the amount of the charged particle at inside of the film thickness measuring region and the average value of the amount of the charged particle at inside of the reference region, or the average value of the luminance of the film thickness measuring region and the average value of the luminance of the reference region, a variation in the calculated value when measured by a plurality of times can be restrained.

Operation by the sixth problem resolving means is as follows. By calculating the average value from the amounts of the charged particles or the luminances of the plurality of reference regions and calculating the calculated value by using the average value, the variation in the calculated value when measured by the plurality of times can be restrained.

Operation by the seventh problem resolving means is as follows. By calculating the average value from the amounts of the charged particles or the luminances of the plurality of film thickness measuring regions and calculating the calculated value by using the average value, the variation in the calculated value when measured by the plurality of times can be restrained.

Operation by the eighth problem resolving means is as follows. By calculating the film thicknesses of the plurality of film thickness measuring regions, the film thicknesses of a plurality of portions at inside of the thin film face can be investigated.

Operation by the ninth problem resolving means is as follows. Insides of respective regions of the film thickness measuring region and the reference region are constituted by the single material, thereby, even when the regions are positionally shifted in the standard thin film sample and the thin film sample, the film thicknesses can be measured without being influenced thereby.

Operation by the thirteenth problem resolving means is as follows. By calculating the calculated value constituted by the amount of the charged particle detected at the film thickness measuring region and the amount of the charged particle detected at the reference region and calculating the film thickness of the film thickness measuring region from the calculated value and the calibration data, even when the current amount of the irradiated charged particle beam is varied, the film thickness of the sample formed into the thin film by the focused ion beam machining can be calculated without being influenced thereby.

Operation of the fourteenth problem resolving means is as follows. By calculating the amount of the focused ion beam necessary for reaching the desired film thickness from the calibration data showing the relationship between the amount of irradiating the focused ion beam and the film thickness to be etched and the film thickness of the film thickness measuring region, the amount of irradiating the focused ion beam necessary for etching until reaching the desired film thickness can be acquired.

Operation by the fifteenth problem resolving means is as follows. By providing the first calculating means for calculating the calculated value constituted by the amounts of the charged particles or the luminances of the plurality of regions and the second calculating means for calculating the film thickness of the film thickness measuring region from the calibration data and the calculated value in the apparatus of measuring a thin film sample, even when the current amount of the charged particle beam to be irradiated is varied, the film thickness of the film thickness measuring region can be acquired without being influenced thereby.

Operation by the nineteenth problem resolving means is as follows. By providing the first calculating means for calculating the calculated value constituted by the amounts of the charged particles or the luminances of the plurality of regions and the second calculating means for calculating the film thickness of the film thickness measuring region from the calibration data and the calculated value in the apparatus of fabricating a thin film sample, even when the current amount of the irradiated charged particle beam is varied, the film thickness of the sample formed into the thin film by the focused ion beam machining can be calculated without being influenced thereby.

Operation by the twentieth problem resolving means is as follows. By providing the first calculating means for calculating the calculated value constituted by the amounts of the charged particles or the luminances of the plurality of regions, the second calculating means for calculating the film thickness of the film thickness measuring region from the calibration data and the calculated value, and the third calculating means for calculating the amount of the focused ion beam necessary for reaching a desired film thickness from the calibration data showing the relationship between the amount of irradiating the focused ion beam and the film thickness to be etched and the film thickness of the film thickness measuring region in the apparatus of fabricating a thin film sample, even when the current amount of the charged particle beam to be irradiated is varied, the film thickness of the sample formed into the thin film by the focused ion beam machining can be calculated, further, the amount of irradiating the focused ion beam necessary for machining to reach the desired film thickness can be acquired.

As described above, according to the method and the apparatus of measuring a thin film sample as well as the method and the apparatus of fabricating a thin film sample, it can be provided that even when the current amount of the charged particle beam to be irradiated is varied, the film thickness can be measured accurately, in a short period of time and easily. Further, the film thickness can accurately be measured without being influenced by variation of the current amount of the charged particle beam to be irradiated even when the plurality of samples are measured for a long period of time by calculating the film thickness by using the calculated value uniquely determined by the film thickness of the film thickness measuring region without depending on the current amount of the charged particle beam to be irradiated.

Further, the film thickness of the sample formed into the thin film by the focused ion beam can accurately be measured even when the current amount of the charged particle beam to be irradiated is varied, and therefore, an end point of the focused ion beam machining can accurately be detected.

Further, the film thickness of the sample formed into the thin film by the focused ion beam can accurately be measured even when the current amount of the charged particle beam to be irradiated is varied, the amount of irradiating the focused ion beam necessary for reaching the desired film thickness can be calculated, and therefore, a number of times of confirming the film thickness in an operation of forming into the thin film by the focused ion beam can be reduced, and therefore, the thin film sample can be measured in a short period of time and accurately.

Further, by designating the film thickness measuring region from an image of the charged particle displayed on the display member, the film thickness can be investigated at an arbitrary region at inside of the image of the charged particle.

Further, the film thickness can further accurately be measured by using the average value of the amounts of the charged particle or the luminances of the thin film region or the average value of the amounts of the charged particles or the luminances of the reference region.

Further, the film thickness can further accurately be measured by designating the plurality of reference regions and using the average value of the amounts of the charged particles or the luminances of portions of the plurality of designated reference regions.

Further, the film thickness can further accurately be measured by designating the plurality of film thickness measuring region and using the average value of the amounts of the charged particles or the luminances of portions of the plurality of designated film thickness measuring regions.

Further, by designating portions of the plurality of film thickness measuring regions and calculating the film thicknesses of the plurality of designated film thickness measuring regions, the film thicknesses of the plurality of portions at inside of the thin film face can be investigated, and information with regard to a film thickness distribution at inside of the thin film face can be acquired.

Further, by designating that insides of respective regions of the film thickness measuring region and the reference region to be constituted by the single material, even when the regions are positionally shifted, the film thickness can accurately be measured without being influenced thereby.

Further, the film thickness can be measured even when there is not a portion on which an electron beam impinges on a back side of the film thickness measuring region, by using a reflected electron. Further, the film thickness can be measured efficiently without interrupting machining, since the film thickness can be measured even in machining into the thin film, since an influence of the second electron generated by the machining beam of the focused ion beam or the like is not effected.

BRIEF DESCRIPTION OF THE DRAWINGS

FIG. 2 illustrates schematic views of a sample showing a film thickness measuring method of a background art.

FIG. 3 illustrates views of relationships between a film thickness and a secondary electron amount showing a film thickness measuring method of a background art.

FIG. 4 illustrates schematic views of a sample showing an embodiment of the invention.

FIG. 7 illustrates schematic views of a sample showing an embodiment of the invention.

FIG. 8 is a flowchart of fabricating a thin film sample showing an embodiment of the invention.

FIG. 13 illustrates schematic views of a device sample showing an embodiment of the invention.

FIG. 14 illustrates schematic views of a sample showing an embodiment of the invention.

FIG. 15 illustrates schematic view of a sample showing an embodiment of the invention.

DETAILED DESCRIPTION OF THE PREFERRED EMBODIMENTS

An embodiment of the invention will be explained in reference to FIG. 1 through FIG. 17 as follows.

A method and an apparatus of measuring a thin film sample will be explained in reference to FIG. 1 through FIG. 5. Here, an electron beam is used as a charged particle beam.

Figure 1:
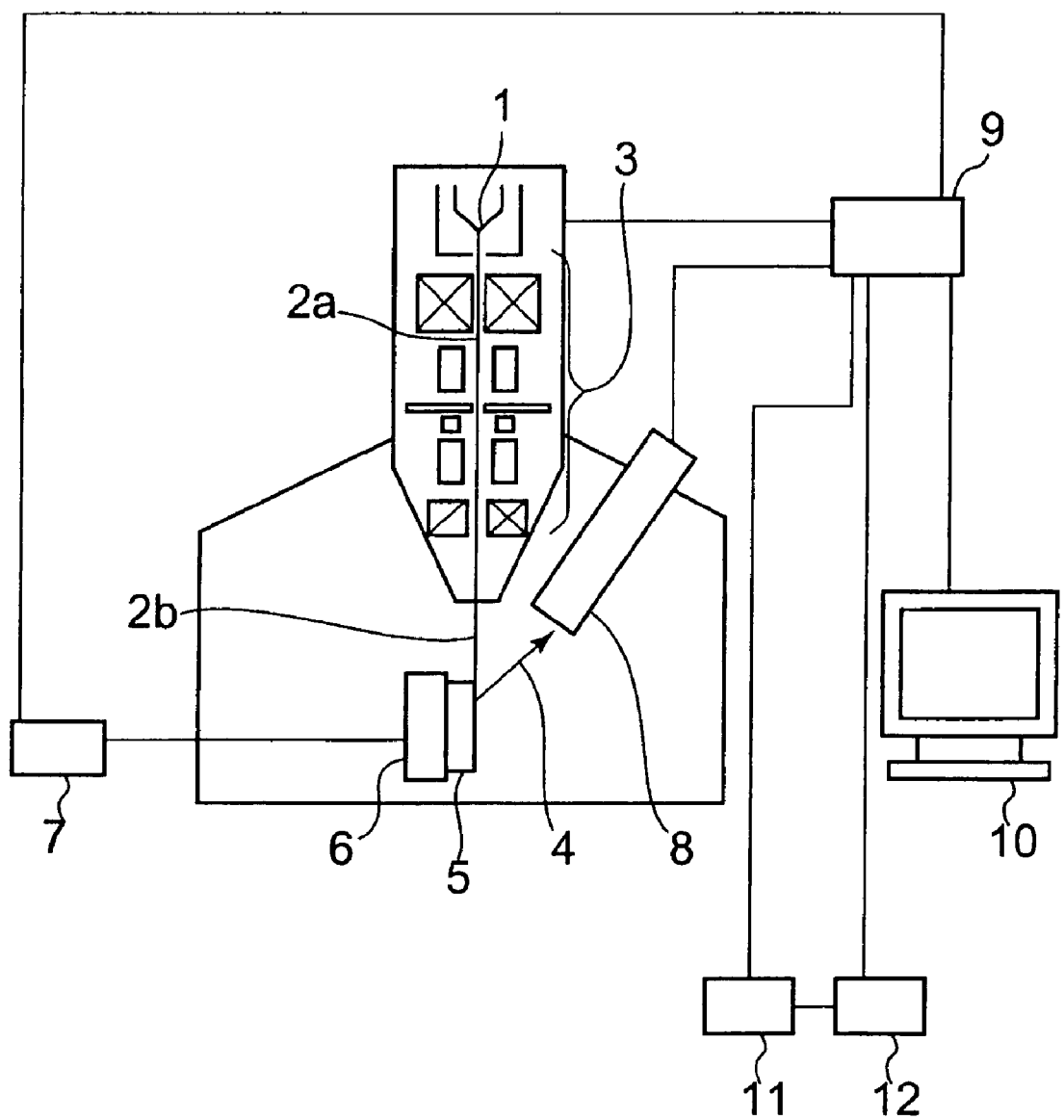
FIG. 1 is an outline view of a thin film sample measuring apparatus showing an embodiment of the invention.

FIG. 1 is an outline view of a thin film sample measuring apparatus showing an embodiment of the invention. The electron 2a generated at the electron generating source 1 is slenderly narrowed by the electron optical system 3 to be the electron beam 2b and is scanned to be irradiated onto the sample 5. The sample 5 is supported by the sample base 6 and can be moved by the sample base controlling means 7. The secondary electron 4 generated by irradiating the electron beam 2b to the sample 5 is detected by the secondary electron detector 6. The detected secondary electron is converted into a luminance signal to display a secondary electron image on the display member 10. Further, calculated values constituted by secondary electron amounts or luminances of a plurality of regions are calculated by the first calculating means 11. Further, a film thickness of the film thickness measuring region is calculated by the second calculating means 12 from the calculated value and a calibration data.

Figure 2A:
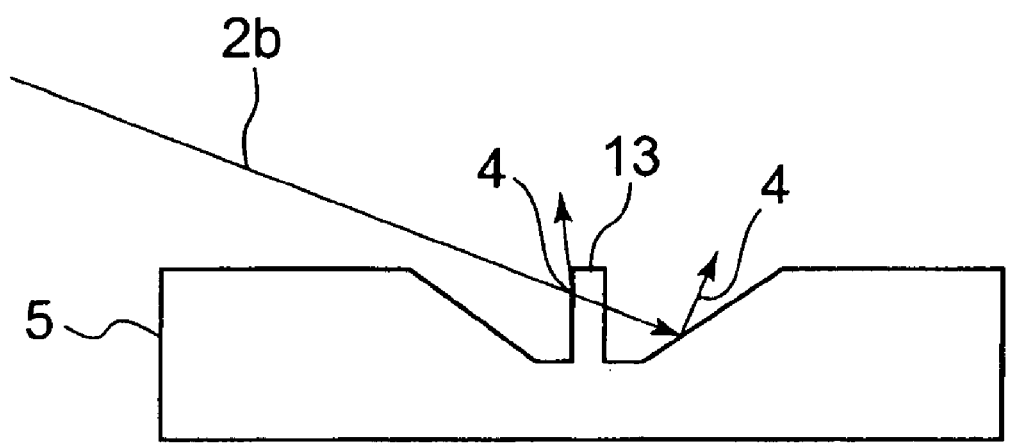
FIG. 2A is a schematic view of a sample.
Figure 2B:
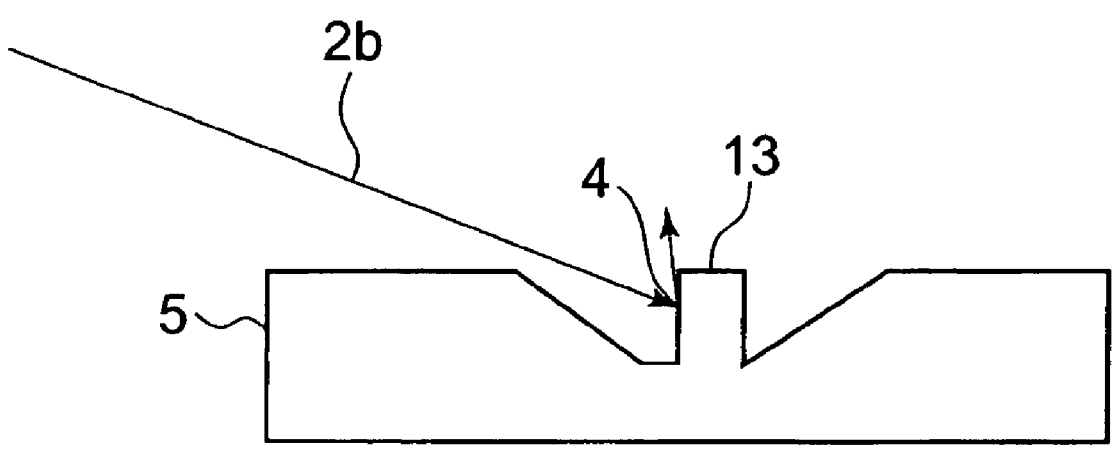
FIG. 2B is a schematic view of a sample.
Figure 3A:
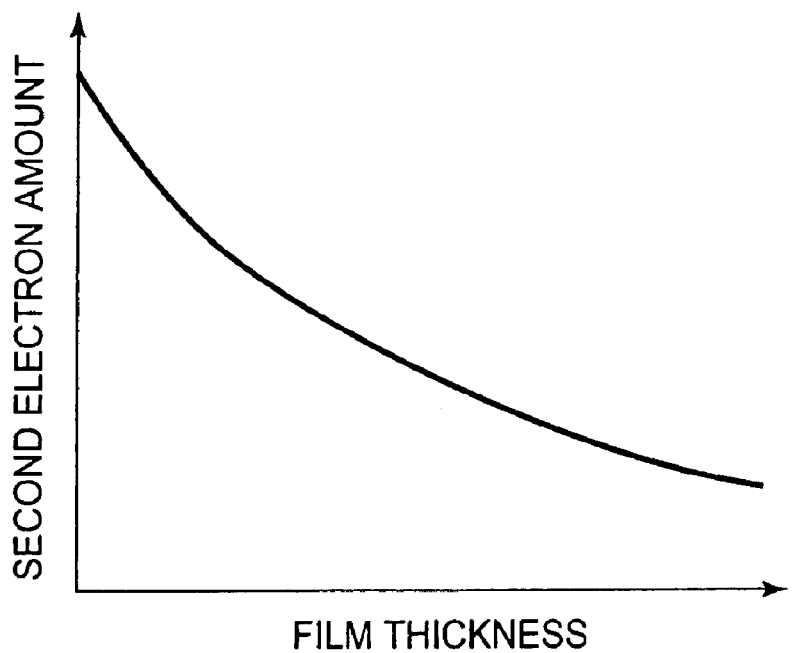
FIG. 3A shows a relationship between a film thickness and a secondary electron amount.
Figure 3B:
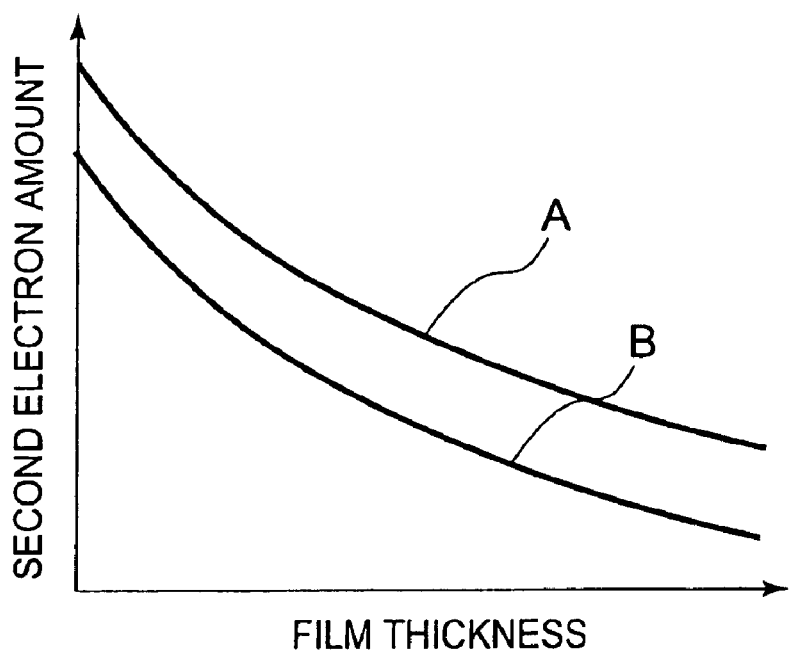
FIG. 3B shows a relationship between a film thickness and a secondary electron by a different electron beam current.

FIG. 2 illustrates schematic views of a sample showing a film thickness measuring method of a background art. When a film thickness of the thin film portion 13 is thin, as shown by FIG. 2A, the electron beam 2b is incident on the sample 5 by transmitting the thin film portion 13. At this occasion, the secondary electrons 4 are generated from a surface of the thin film portion 13 and the sample 5. On the other hand, when the film thickness of the thin film portion 13 is thick, as shown by FIG. 2B, the electron beam 2b cannot transmit the thin film portion 13. At this occasion, the secondary electron 4 is generated only from the surface of the sample. FIG. 3 illustrates diagrams of a relationship between a film thickness and a secondary electron amount showing a film thickness measuring method of a background art. FIG. 3A is a graph of the film thickness of the thin film portion 13 and a detected secondary electron amount. It is known that the smaller the film thickness, the larger the secondary electron amount. As shown by FIG. 2, it seems that when the film thickness is thin, the electron beam 2b is incident on the sample 5 by transmitting the thin film portion 13 and the secondary electrons are generated from the sample 5 and the thin film portion 13, and therefore, the secondary electron amount to be detected is increased. It has been confirmed by an experiment that the secondary electron amount is not linearly reduced relative to the film thickness. This seems to be caused by that when the electron beam transmits the thin film portion 13, there is an energy loss, and therefore, an energy of an electron incident on the sample 5 is changed by the film thickness of the thin film portion 13. Meanwhile, it is known that the relationship between the film thickness and the secondary electron amount is as shown by FIG. 3B when a current amount of the electron beam 2b differs. Notation A in the drawing designates a case in which the electron beam current amount is large and notation B designates a case in which the electron beam amount is small. It is known thereby that when the film thickness of the desired sample is measured based on the calibration data, unless the film thickness of the desired sample is measured by a current amount the same as a current amount of an electron beam of measuring the calibration data, an error is brought about in the measured film thickness.

Figure 4A:
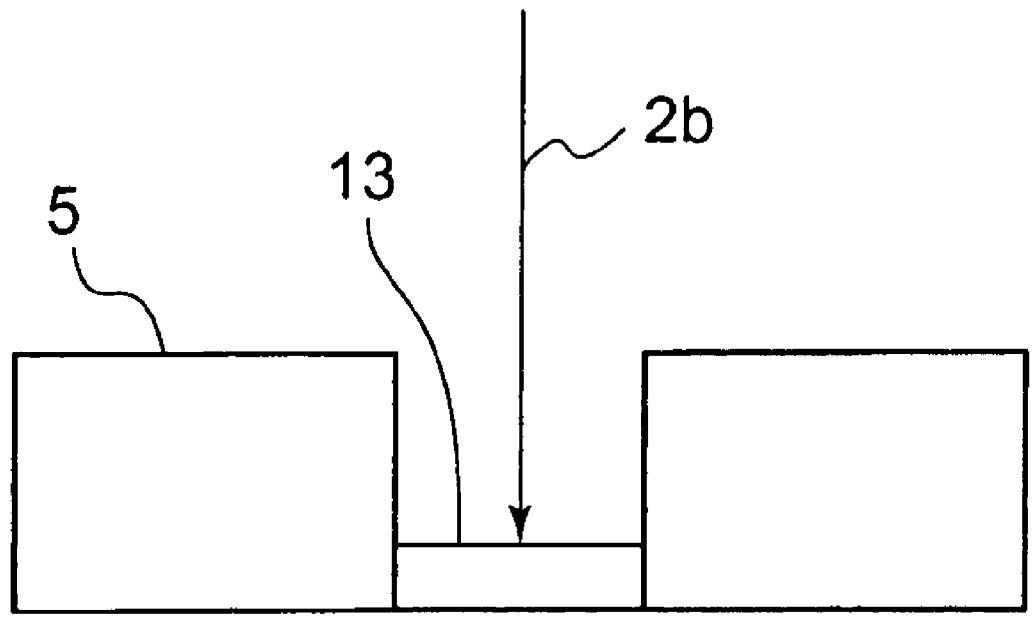
FIG. 4A is a schematic view of a sample.
Figure 4B:
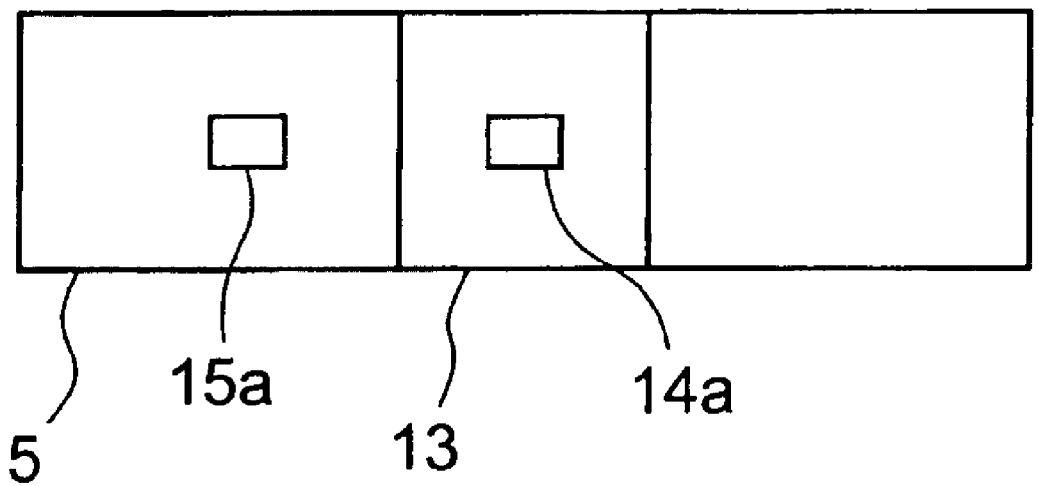
FIG. 4B is a top view.
Figure 5:
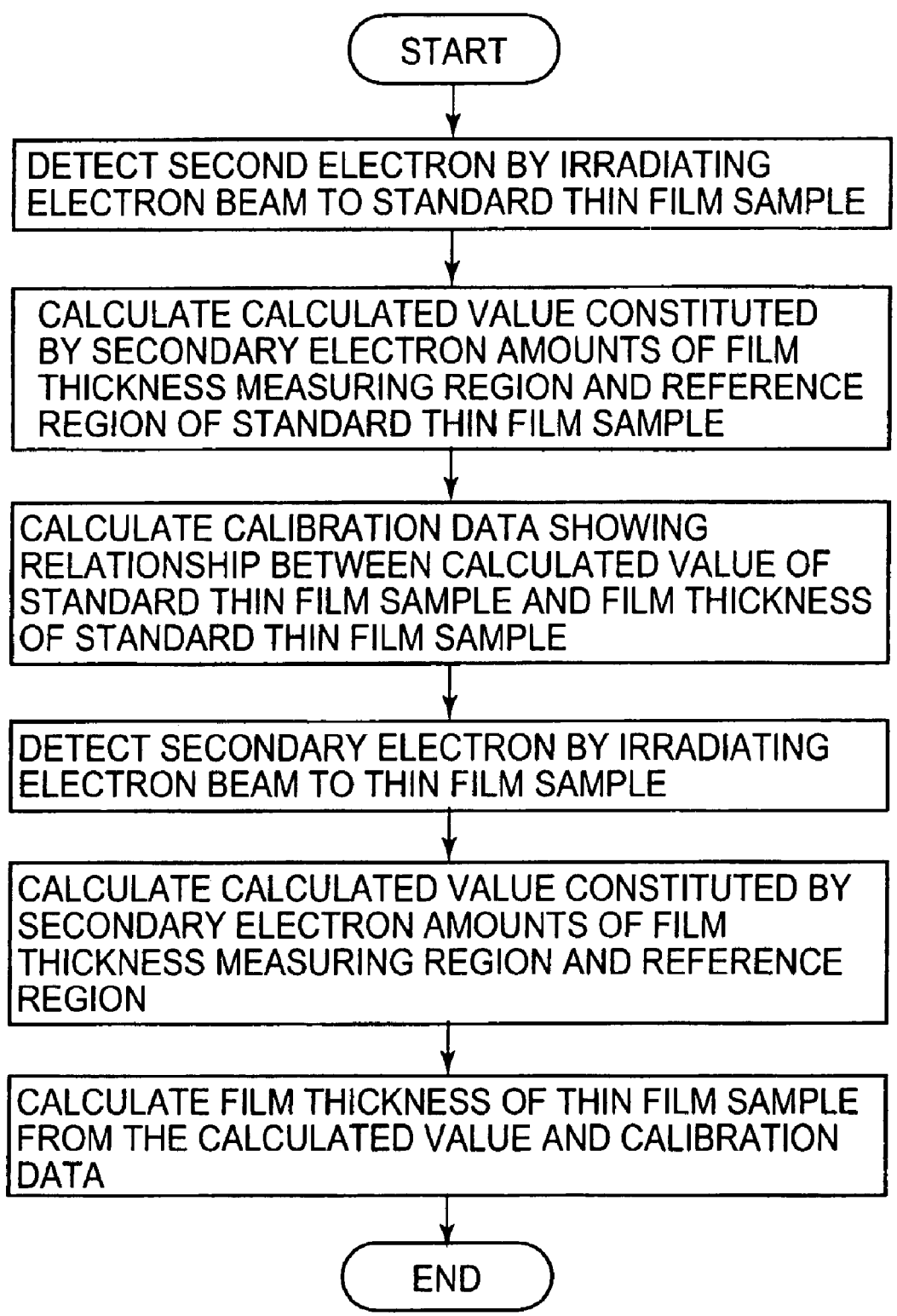
FIG. 5 is a flowchart of measuring a thin film sample showing an embodiment of the invention.

FIG. 4 illustrates schematic views of a sample showing an embodiment of the invention, FIG. 4A is a schematic view of a sample, and FIG. 4B is a top view viewed from a direction of irradiating the electron beam 2b of FIG. 4A. When the electro beam 2b transmits the thin film portion 13, a portion on which the transmitted electron beam 2b impinges is present although not illustrated here. A film thickness measuring method will be explained in accordance with a flowchart of measuring a thin film sample showing an embodiment of the invention of FIG. 5. First, the calibration data is formed by using a standard thin film sample which is a portion having a material the same as that of the thin film sample for measuring the film thickness or the same as that of the same device and the film thickness is known. The electron beam 2b is irradiated to a region including a thin film portion of a standard thin film sample and the generated secondary electron 4 is detected by the secondary electron detector 6. By using amounts of secondary electrons generated at a film thickness measuring region and a reference region at inside of the thin film portion, a calculated value constituted by an amount of secondary electrons detected at the film thickness measuring region and an amount of secondary electrons detected at the reference region is calculated by the first calculating means 11. The step is carried out by standard thin film samples having a plurality of film thickness. A calibration data is formed from a calculated relationship between the calculated value and the film thickness of the standard thin film sample. Next, when the film thickness of the thin film portion 13 of the sample is measured, the electron beam 2b is irradiated to the region including the thin film portion 13, and the generated electron 4 is detected by the secondary electron detector 6. By using the amounts of secondary electrons generated at the film thickness measuring region 14a at inside of the thin film portion 13 and the reference region 15a of a thick portion of the sample 5, a calculated value constituted by the amount of the secondary electrons detected at the film thickness measuring region 14a and the amount of the secondary electrons detected at the reference region 15a is calculated by the first calculating means 11. Here, the calculated value of the amount of the secondary electrons detected at the film thickness measuring region 14a and the amount of the secondary electrons generated at the reference region 15a constitutes a function of an amount of secondary electrons generated by the electron beam 2b having the same beam current amount. That is, the function is a function uniquely determined by the film thickness of the film thickness measuring region 15a which does not depend on the current amount of the irradiated electron beam. Therefore, even when the amounts of the beam currents of the electron beams irradiated to the thin film measuring sample and the standard thin film sample differ from each other, the calculated value stays the same value when the film thickness is the same. Therefore, even when the current amount of the irradiated electron beam 2b is varied, the calculated value is not effected with an influence thereof. The film thickness of the film thickness measuring region 14a can be calculated from the calibration data showing the relationship between the calculated value of the standard thin film sample and the film thickness of the standard thin film sample and the calculated value calculated from the sample 5. Here, an arrangement of the secondary electron detector 8 effects an influence on the secondary electron amount, and therefore, in measuring the standard thin film sample and measuring the thin film sample, the arrangement of the secondary electron detector 8 is made to remain unchanged.

Next, an explanation will be given of a method and an apparatus of fabricating a thin film sample for forming a portion of a wafer sample into a thin film by a focused ion beam and measuring a film thickness of a thin film portion in reference to FIG. 6, FIG. 7, and FIG. 8.

Figure 6:
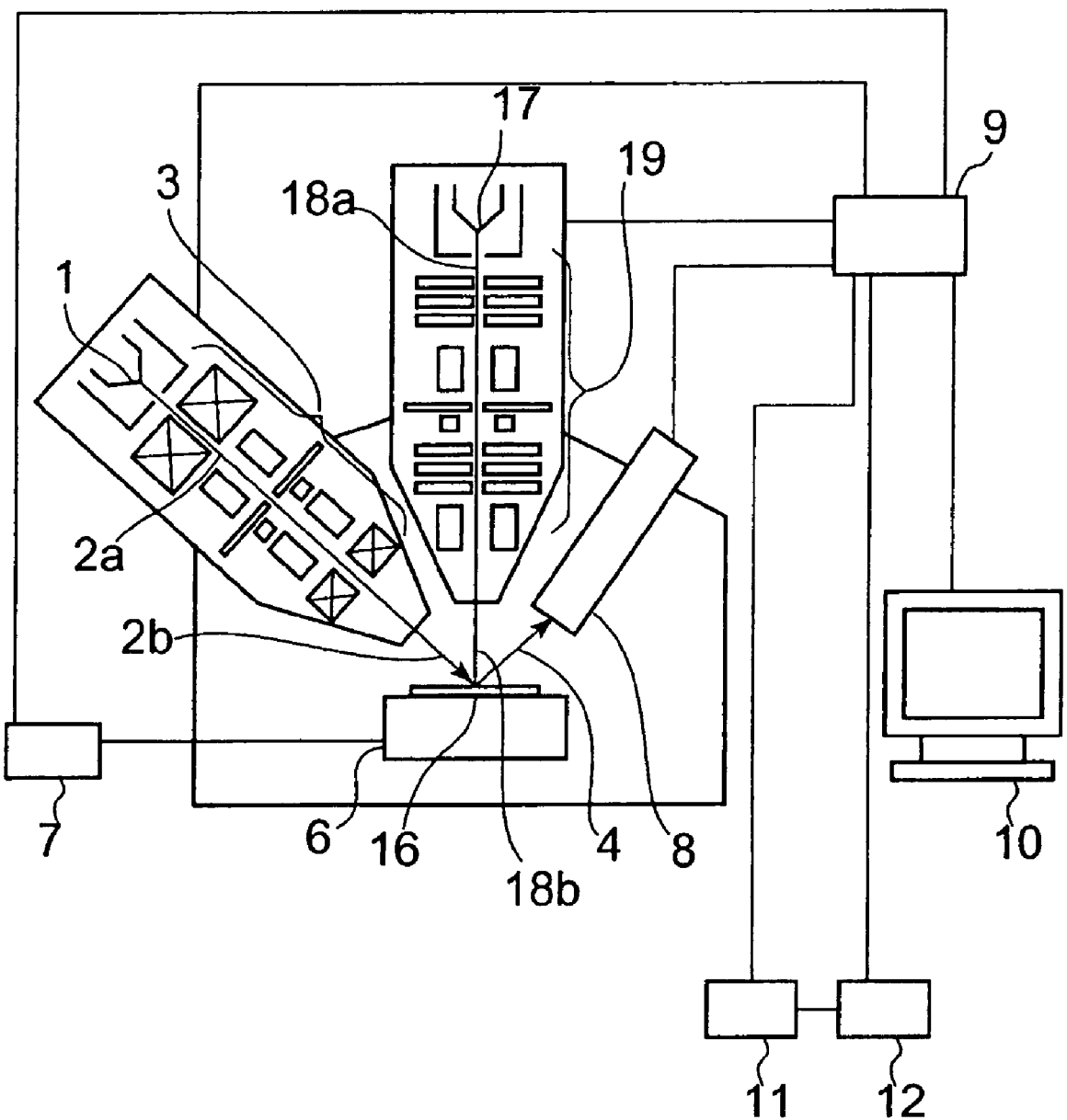
FIG. 6 is an outline view of a tin film sample fabricating apparatus showing an embodiment of the invention.

FIG. 6 is an outline view of a thin film sample fabricating apparatus showing an embodiment of the invention. The ion 18a generated by the ion generating source 17 is slenderly narrowed by the ion optical system 19 to be the ion beam 18b and is scanned to irradiate onto the sample 5. Further, the electron 2a generated by the electron generating source 1 is slenderly narrowed by the electron optical system 3 to be the electron beam 2b and is scanned to irradiate onto the wafer 16 constituting the sample. The wafer 16 is supported by the sample base 6 and can be moved by the sample base controlling means 7. The secondary electron 4 generated by irradiating the ion beam 18b or the electron beam 2b on the wafer 16 is detected by the secondary electron detector 8. The detected secondary electron is converted into a luminance signal to display a secondary electron image on the display member 10. Further, calculated values constituted by secondary electron amounts or luminances of a plurality of regions are calculated by the first calculating means 11. Further, the film thickness of the film thickness measuring region is calculated by the second calculating means 12 from the calculated values and the calibration data. Although in FIG. 6, there is constituted an arrangement in which when the sample is horizontally installed, the ion beam 18b is vertically incident on the wafer and the electron beam 2b is obliquely incident thereon, the arrangement of the ion beam 18b and the electron beam 2b may be reversed.

Figure 7A:
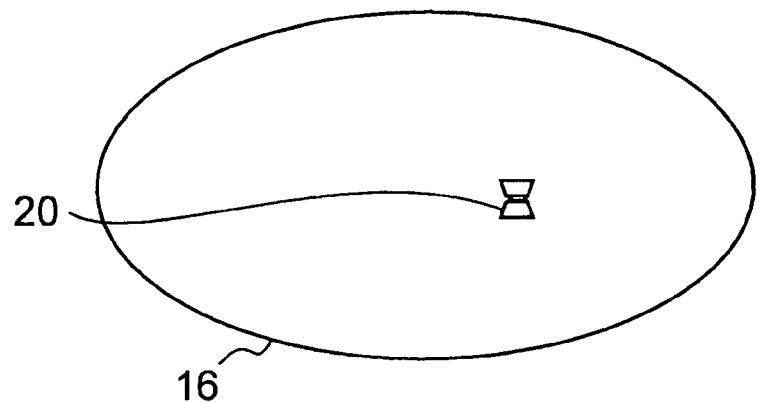
FIG. 7A is a schematic view of a wafer.
Figure 7B:
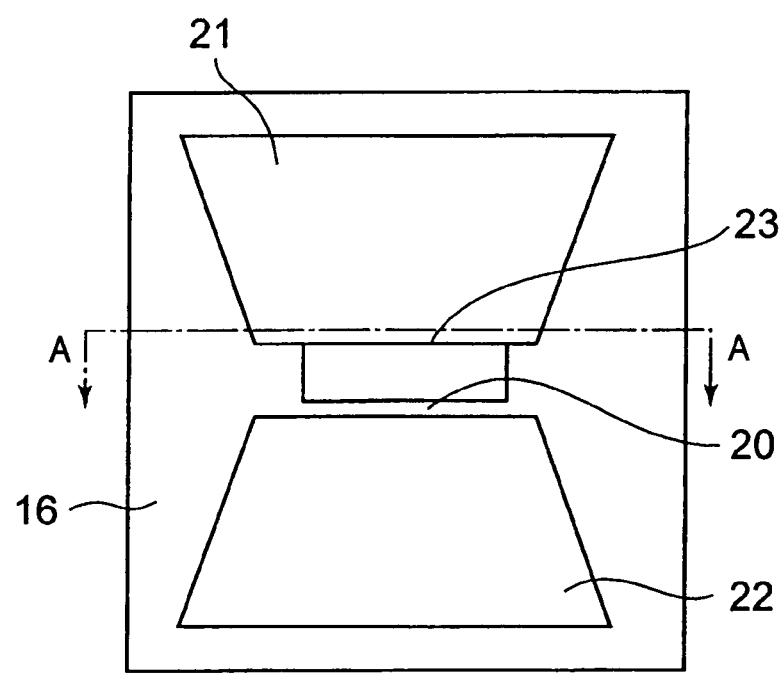
FIG. 7B is a view of a periphery of a region formed into a thin film.
Figure 7C:
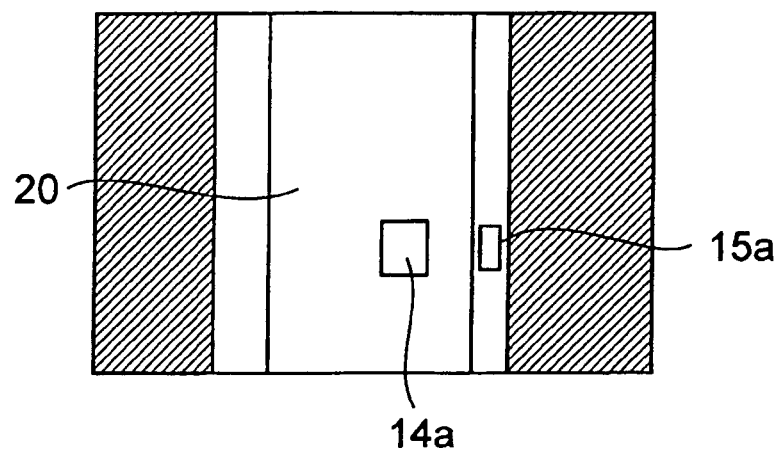
FIG. 7C is a sectional view taken along a line A-A.

FIG. 7 illustrates schematic views of a sample showing an embodiment of the invention for explaining a method of forming a portion of the wafer 16 into a thin film. FIG. 7A illustrates schematic views of a wafer 16. A region constituting a portion of the wafer 16 and formed into a thin film is the thin-filmed region 20. An explanation will be given of a method of fabricating a thin film sample in accordance with a flowchart of fabricating a thin sample showing an embodiment of the invention of FIG. 8. First, a calibration data showing a relationship between a calculated value of a standard thin film sample and a film thickness of the standard thin film sample is formed by using a standard thin film sample similar to that of the above-described film thickness measuring method. FIG. 7B is a view of a periphery of a thin-filmed region. The machined groove 22 is formed at the surface of the wafer 16 and on one side of a vicinity of the thin-filmed region 20 by etching by the ion beam 18b. Successively, the machined groove 21 is formed at the surface of the sample on a side opposed to the machined groove 22 by interposing the thin-filmed region 20 by etching by the ion beam 18b. Next, a portion of the wafer is formed into a thin film by forming the machined groove 23 by etching by scanning to irradiate the ion beam 18b such that a desired film thickness is constituted at the thin-filmed region 20. FIG. 7C is a sectional view taken along a line A-A of FIG. 7B. The electron beam 2b is irradiated to the region of the thin-filmed region 20 including the surface of the thin film, and the generated secondary electron 4 is detected by the secondary electron detector 8. By using amounts of secondary electrons generated at the film thickness measuring region 14a at inside of the thin-filmed region 20 and the reference region 15a disposed at outside of the thin-filmed region 20, a calculated value constituted by the amount of secondary electrons detected at the film thickness measuring region 14a and the amount of secondary electrons detected at the reference region 15a is calculated by the first calculating means 11. Further, the film thickness of the film thickness measuring region 14a can be calculated from the calibration data showing the relationship between the calculated value of the standard film thickness sample formed initially and the film thickness of the standard thin film sample, and the calculated value calculated at the thin-filmed region 20. Further, when the calculated film thickness of the film thickness measuring region 14a is thicker than a desired film thickness, by repeating a process of machining the film into a thin film by the focused ion beam 18b and measuring the film thickness by the electron beam 2b again until the desired film thickness is reached, an end point of machining by the focused ion beam is accurately detected and the sample having the desired film thickness can be fabricated.

Figure 10:
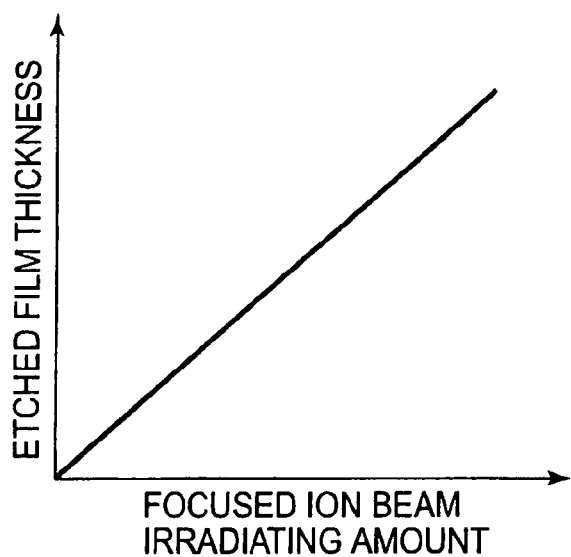
FIG. 10 is a diagram showing a relationship between a focused ion beam irradiating amount and a film thickness to be etched showing an embodiment of the invention.
Figure 11:
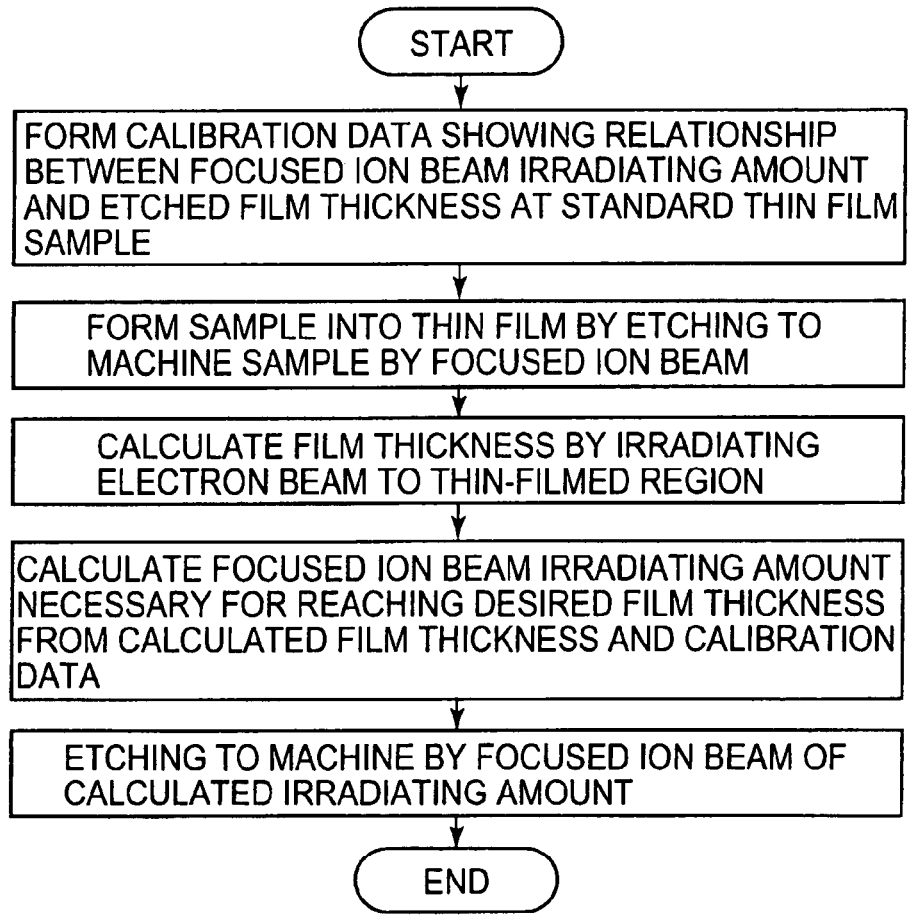
FIG. 11 is a flowchart of fabricating a thin film sample showing an embodiment of the invention.

Next, an explanation will be given of a method and an apparatus of fabricating a thin film sample by forming a sample into a thin film by a focused ion beam, measuring a film thickness of a thin-filmed portion and acquiring an amount of irradiating a focused ion beam necessary for reaching a desired film thickness in reference to FIG. 9, FIG. 10, and FIG. 11.

Figure 9:
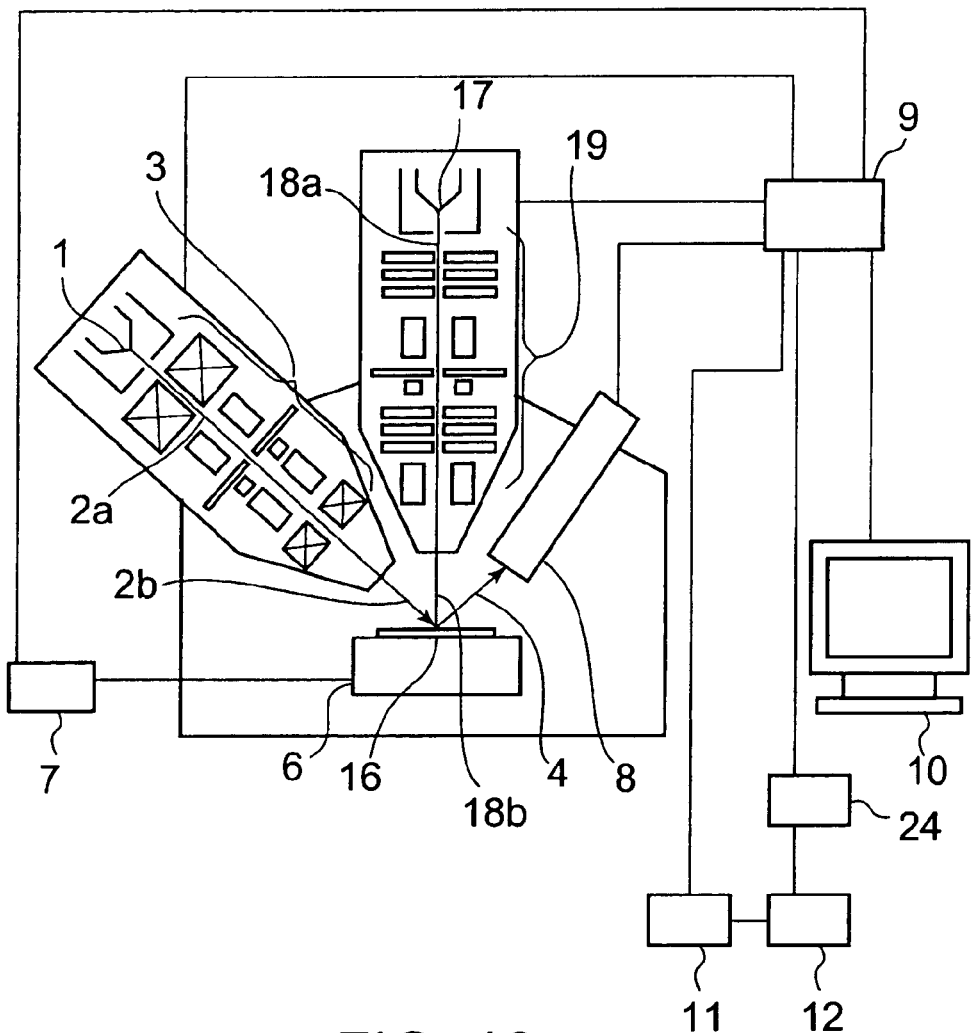
FIG. 9 is an outline view of a thin film sample fabricating apparatus showing an embodiment of the invention.

FIG. 9 is an outline view of a thin film sample fabricating apparatus showing an embodiment of the invention. The ion 18a generated by the ion generating source 17 is slenderly narrowed by the ion optical system 19 to be the ion beam 18b and is scanned to irradiate onto the wafer 16 constituting a sample. Further, the electron 2a generated by the electron generating source 1 is slenderly narrowed by the electron optical system 3 to be the electron beam 2b and is scanned to irradiate onto the wafer 16. The wafer 16 is supported by the sample base 6 and can be moved by the sample base controlling means 7. The secondary electron 4 generated by irradiating the ion beam 18b or the electron beam 2b to the wafer 16 is detected by the secondary electron detector 8. The detected secondary electron is converted into a luminance signal to display a secondary electron image on the display member 10. Further, calculated values constituted by secondary electron amounts or luminances of a plurality of regions are calculated by the first calculating means 11. Further, the film thickness of the film thickness measuring region is calculated by the second calculating means 12 from the calculated values and the calibration data. The amount of irradiating the focused ion beam necessary for reaching the desired film thickness is calculated by the third calculating means 24 from the calibration data showing the relationship between the amount of irradiating the focused ion beam and the film thickness to be etched and the film thickness of the film thickness measuring region. Further, although in FIG. 9, there is constituted an arrangement in which the focused ion beam is vertically incident on the sample and the electron beam is obliquely incident thereon when the sample is horizontally installed, the arrangement of the ion beam and the electron beam may be reversed.

An explanation will be given of a method and an apparatus of fabricating a thin film sample in accordance with a flowchart showing an embodiment of the invention of FIG. 11. The sample is machined to form into a thin film by the focused ion beam similar to the above-described thin film sample fabricating method of forming the sample into the thin film and measuring the film thickness of the thin-filmed portion and the film thickness of the thin-filmed region is measured by the electron beam. Further, the calibration data showing the relationship between the amount of irradiating the focused ion beam and the etched film thickness is acquired by previously using a standard thin film sample. For example, FIG. 10 is a diagram showing a relationship between an amount of irradiating the focused ion beam and the film thickness to be etched showing an embodiment of the invention. As shown by FIG. 10, a correlation is established between the focused ion beam irradiating amount and the film thickness to be etched. Next, the amount of irradiating the focused ion beam necessary for reaching the desired film thickness is calculated by the third calculating means 24 from the calculated film thickness of the film thickness measuring region 14a and the desired film thickness and the calibration data showing the relationship between focused the ion beam irradiating amount and the film thickness to be etched acquired by using the standard thin film sample.

In a background art, a step of carrying out thin film forming machining by the focused ion beam, switching the focused ion beam to the electron beam, measuring the film thickness by irradiating the electron beam to the thin film and carrying out the thin film forming machining again by the focused ion beam when the desired film thickness is not reached is repeatedly carried out until the desired film thickness is reached. However, the amount of irradiating the focused ion beam necessary for reaching the desired film thickness can be calculated as described above, and therefore, the thin film sample having the desired film thickness can be fabricated in a short period of time.

Figure 16:
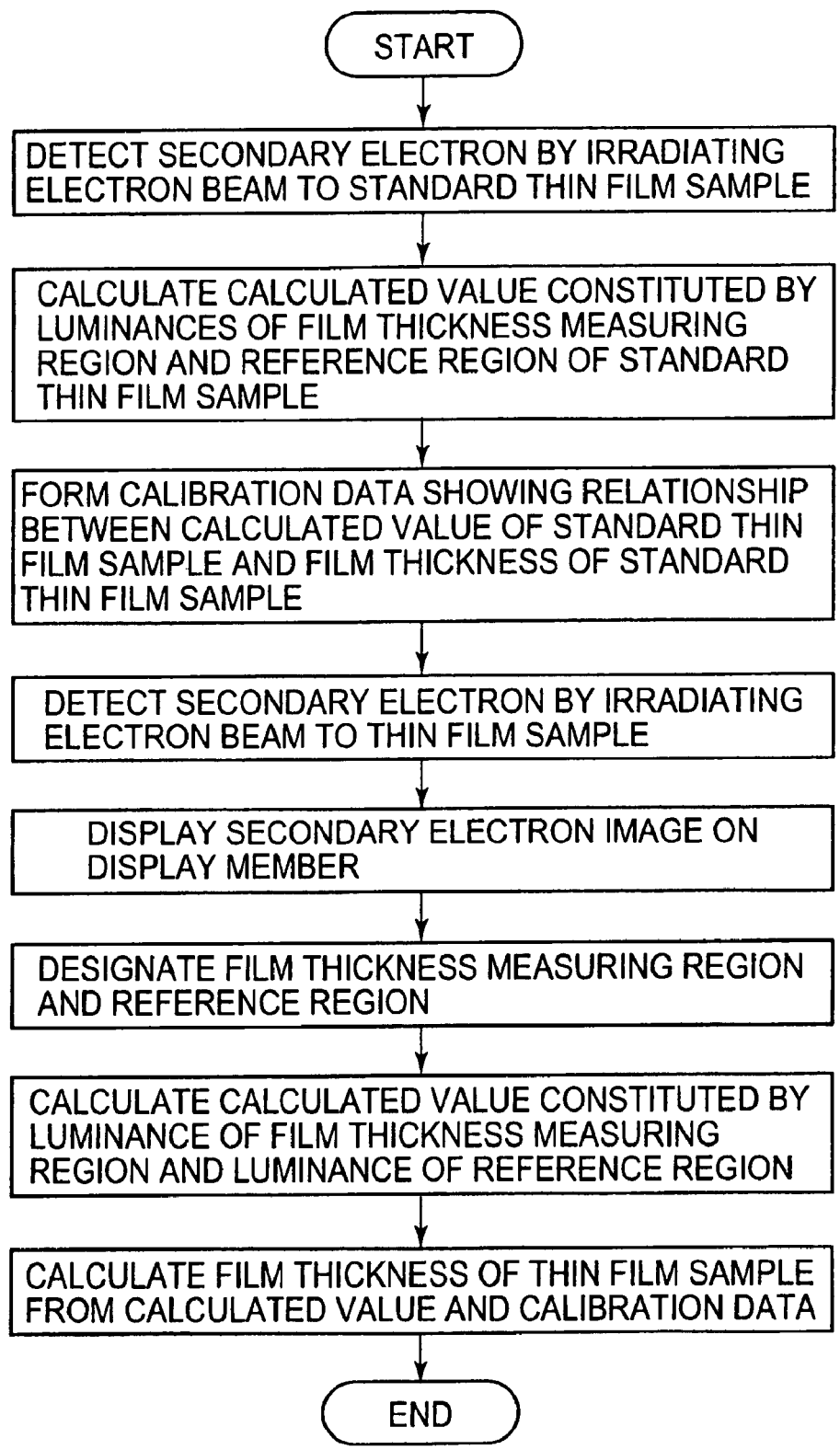
FIG. 16 is a flowchart of measuring a thin film sample showing an embodiment of the invention.

Next, an explanation will be given of a method of measuring a thin film sample using a luminance by using a flowchart of measuring a thin film sample showing an embodiment of the invention of FIG. 4 and FIG. 16.

First, the calibration data showing the relationship between the calculated value of the standard thin film sample and the film thickness of the standard thin film sample is formed by using the standard thin film sample similar to the above-described film thickness measuring method. When the film thickness of the thin-filmed portion 13 of the sample is measured, the electron beam 2b is irradiated to the region including the thin-filmed portion 13 and the generated second electron 4 is detected by the secondary electron detector 8. A secondary electron image is displayed on the display member 10 based on the detected secondary electron 4. By the displayed secondary electron image, the film thickness measuring region 14a is designated at inside of the thin-filmed portion 13 and the reference region 15a is designated to the thick portion of the sample 5. By using luminances of the designated film thickness measuring region 14a and the designated reference region 15a, a calculated value constituted by a luminance of the film thickness measuring region 14a and a luminance of the reference region 15a is calculated by the first calculating means 11. Here, the luminance is constituted by converting a signal of the secondary electron into a brightness displayed on the display member 10 for displaying at the display member 10. Further, a calculated value of the luminance of the film thickness measuring region 14a and the luminance of the reference region 15a constitutes a function of a luminance of the secondary electron image based on the secondary electron 4 generated by the electron beam 2b of the same beam current amount. That is, the function is a function uniquely determined by the film thickness of the film thickness measuring region 14a which does not depend on the current amount of the irradiated electron beam 2b. Therefore, even when amounts of beam currents of the electron beams 2b irradiated to the thin film measuring sample and the standard thin film sample differ from each other, the calculated value stays the same value so far as the film thickness stays the same. Therefore, even when the current amount of the irradiated electron beam 2b is varied, the calculated value is not effected with an influence thereof. Further, the calculated value of the standard thin film sample constituted by the luminance of the thin film measuring region of the standard thin film sample and the luminance of the reference region of the standard thin film sample is calculated by the first calculating means 11. Further, the film thickness of the film thickness measuring region 14a can be calculated from the calibration data showing the relationship between the calculated value of the standard thin film sample and the film thickness of the standard sample and the calculated value calculated at the sample 5. In this way, the film thickness of the film thickness measuring region 14a designated by the secondary electron image displayed on the display member 10 can be investigated. Further, the method can also be used in the thin film sample fabricating method of forming the sample into the thin film by the focused ion beam and measuring the film thickness of the thin-filmed portion, and the thin film sample fabricating method of forming the sample into the thin film by the focused ion beam, measuring the film thickness of the thin-filmed portion, and acquiring the amount of irradiating the focused ion beam necessary for reaching the desired film thickness.

Figure 12:
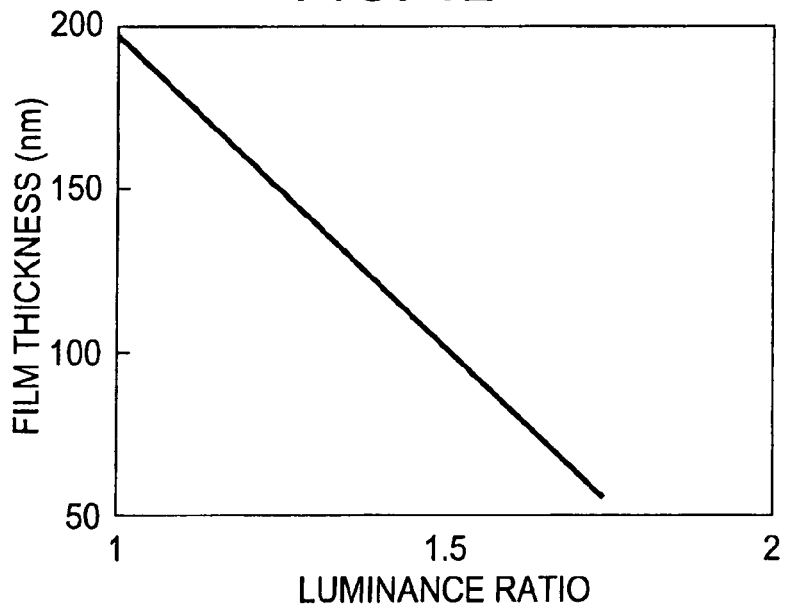
FIG. 12 is a diagram showing a relationship between a luminance ratio and a film thickness showing an embodiment of the invention.

Next, an explanation will be given of a calculated value constituted by a secondary electron amount detected at the film thickness measuring region and a secondary electron amount detached at the reference region, or a luminance of the film thickness measuring region and a luminance of a reference region in reference to FIG. 4 and a diagram showing a relationship between a luminance ratio and a film thickness showing an embodiment of the invention of FIG. 12.

The calculated value constituted by the secondary electron amount detected at the film thickness measuring region 14a and the secondary electron amount detected at the reference region 15a is a function of a secondary electron amount generated by the electron beam 2b of the same beam current amount. The function is a function uniquely determined by the film thickness at the film thickness measuring region 14a without depending on the current amount of the irradiated electron beam 2b. For example, as a calculated value, there is conceivable a ratio of the secondary electron amount detected at the film thickness measuring region 14a to the secondary electron amount detected at the reference region 15a. When the calculated value is designated by notation P, the secondary electron amount detected at the film thickness measuring region 14a is designated by notation I, and the secondary electron amount detected at the reference region 15a is designated by notation I', the calculated value P can be expressed as shown below.

$P=I/I'$

The thinner the thin film portion 13, the more increased the probability of transmitting the irradiated electron beam 2b through the film thickness measuring region 14a. Although not illustrated here, the transmitted electron beam 2b impinges on a portion of the sample disposed on the back side of the thin film portion 13a to generate a secondary electron. Therefore, when the film thickness of the thin film portion 13 is thinned, the secondary electron generated at the film thickness measuring region 15a is increased. On the other hand, at the reference region 15a disposed at a thick portion of the sample 5, a probability of transmitting the irradiated electron beam 2b therethrough remains unchanged, and therefore, the amount of the generated secondary electron remains unchanged. Therefore, the thinner the film thickness of the film thickness measuring region 14a, the more increased the calculated value P. The same goes with the calculated value constituted by the luminance of the film thickness measuring region 14a and the luminance of the reference region 15a, and there is a correlation between the luminance ratio and the film thickness of the film thickness measuring region 14a. FIG. 12 shows a data of a relationship of the luminance ratio and the film thickness acquired by the inventors by an experiment. Although an explanation has been given here of the ratio of the secondary electron amounts, the luminance may be used in place of the secondary electron amount.

Next, an explanation will be given of a step of calculating the calculated value constituted by the secondary electron amount detected at the film thickness measuring region and the secondary electron amount detected at the reference region, or the luminance of the film thickness measuring region and the luminance of the reference region in reference to FIG. 4, a schematic view of a device sample showing an embodiment of the invention of FIG. 13, a schematic view of a sample showing an embodiment of the invention of FIG. 14, and a schematic view of a sample showing an embodiment of the invention of FIG. 15.

In FIG. 4, when the film thickness measuring region 14a and the reference region 15a are regions constituted by a plurality of electron beam irradiating points, by calculating an average value of the secondary electron amounts or the luminances of the film thickness measuring region 14a and the reference region 15a, the calculated value constituted by the secondary electron amount detected at the film thickness measuring region 14a and the secondary electron amount detected at the reference region 15a, or the luminance of the film thickness measuring region 14a and the luminance of the reference region 15a can restrain a variation in the calculated value when measured by a plurality of times, and the film thickness of the film thickness measuring region 14a can accurately be measured.

Figure 15A:
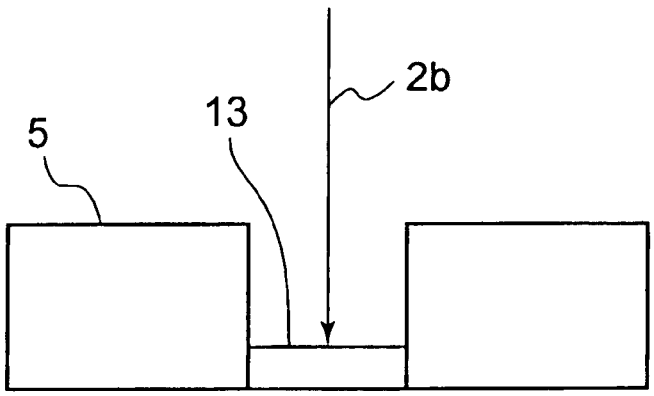
FIG. 15A is a schematic view of a sample.
Figure 15B:
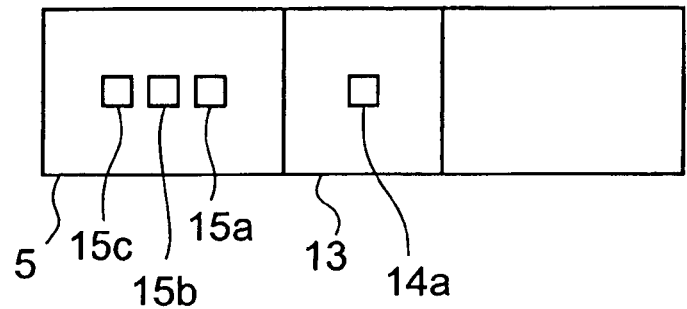
FIG. 15B is a top view.

Further, in FIG. 15, by calculating the calculated value constituted by the secondary electron amount detected at the film thickness measuring region 14a and an average value of secondary electron amounts or luminances detected at a plurality of the reference regions 15a, 15b, 15c by using an average value or an average luminance of secondary electron amounts detected by a plurality of the reference regions 13a, 13b, 13c of a thick portion of a sample 5, a variation in the calculated value when measured by a plurality of times can be restrained, and the film thickness of the film thickness measuring region 14a can accurately be measured.

Figure 14A:
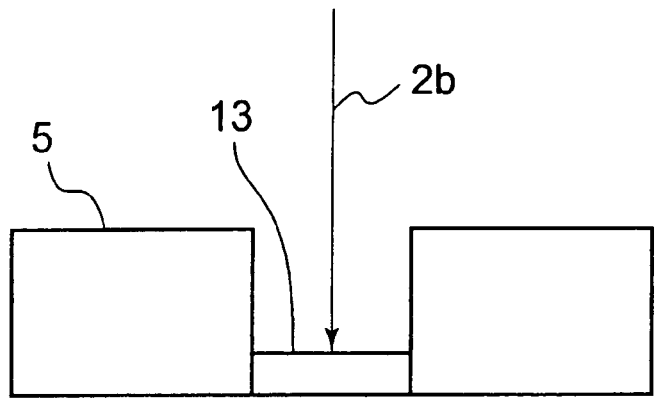
FIG. 14A is a schematic view of a sample.
Figure 14B:
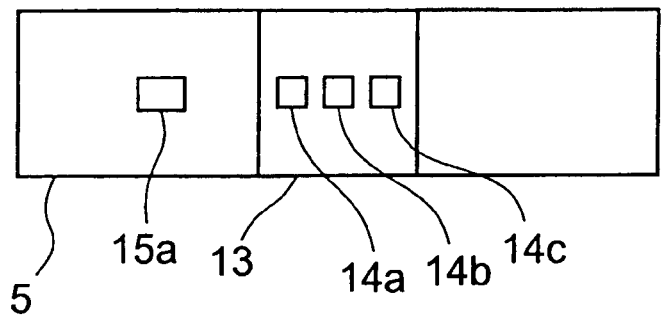
FIG. 14B is a top view.

Further, in FIG. 14, by calculating a calculated value constituted by an average value of secondary electron amounts detected at a plurality of the film thickness measuring regions 14a, 14b, 14c and a secondary electron amount detected at the reference region 15a, or an average luminance of a plurality of the film thickness measuring regions 14a, 14b, 14c and a luminance of the reference region 15a by using an average value of the secondary electron amounts or the luminances detected at the plurality of film thickness measuring regions 14a, 14b, 14c of the thin film portion 13, a variation in the calculated value when measured by a plurality of times can be restrained, and the film thickness of the thin film portion 13 can accurately be measured.

Further, in FIG. 14, by calculating a calculated value constituted by the secondary electron amounts respectively detected at the plurality of film thickness measuring regions 14a, 14b, 14c and the secondary electron amount detected at the reference region 15a, or respective luminances of the plurality of film thickness measuring regions 14a, 14b, 14c and the luminance of the reference region 15a by using the plurality of film thickness measuring regions 14a, 14b, 14c of the thin film portion 13, film thicknesses of the plurality of portions 14a, 14b, 14c of the thin film portion 13 can be acquired and a film thickness distribution at inside of the thin film portion 13 can be investigated.

Figure 13A:
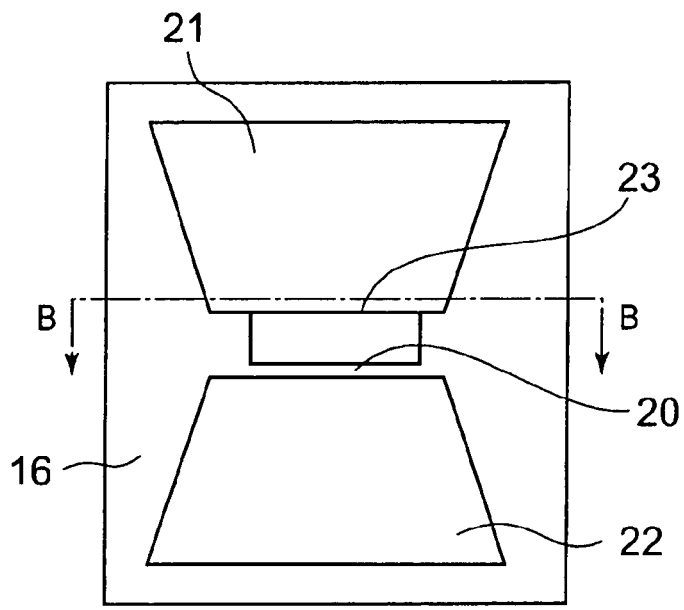
FIG. 13A is a view of a surface of a sample.
Figure 13B:
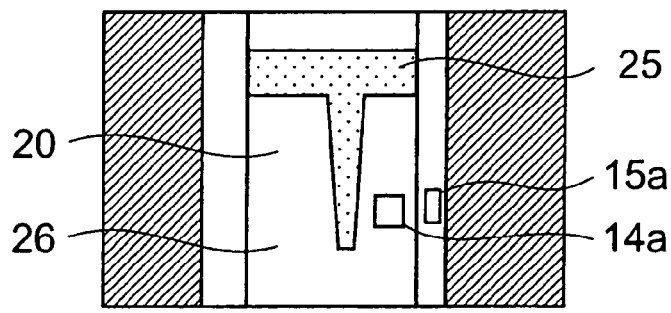
FIG. 13B is a sectional view taken along a line B-B.
Figure 13C:
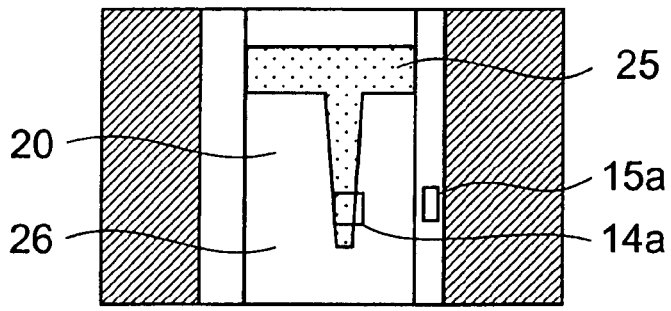
FIG. 13C is a sectional view taken along the line B-B.
Figure 13D:
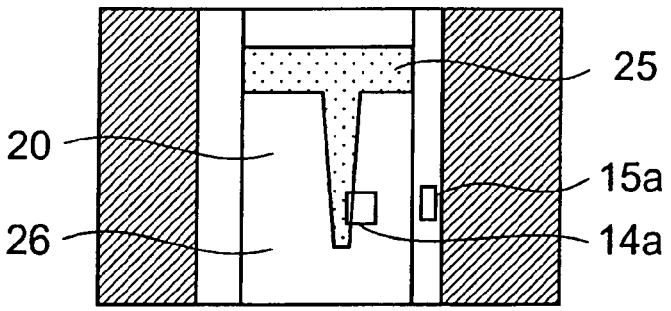
FIG. 13D is a sectional view taken along the line B-B.

Further, FIG. 13 illustrates schematic views of a device comprising a wiring material 25 and an insulating material 26, FIG. 13A is a view of a surface of a sample, FIGS. 13B, 13C, 13D are sectional views taken along a line B-B of FIG. 13A. In FIGS. 13C, 13D, at the film thickness measuring region 14a, the wiring material 25 is included in the film thickness measuring region other than the insulating material 26. At the film thickness measuring region 14a of FIG. 13C, a rate of including the insulating material 26 and the wiring material 25 at the film thickness measuring region 14a differs from that of the film thickness measuring region 14a of FIG. 13D. A secondary electron generating efficiency by irradiating an electron beam differs by a material, and therefore, at the film thickness measuring regions 14a of FIGS. 13C, 13D, amounts of generating secondary electrons differ from each other even when an electron beam having the same current amount is irradiated. For example, in the film thickness measuring method, assume that the film thickness measuring region when the calibration data is acquired is the film thickness measuring region 14a of FIG. 13C. Further, assume that a region of measuring a film thickness is deviated by a drift of the irradiated electron beam or the sample base and the film thickness measuring region becomes the film thickness measuring region 14a of FIG. 13D. Then, at the film thickness measuring regions 14a of FIG. 13C, 13D, even when the electron beams having the same current amount are irradiated, the amounts of the generated secondary electrons differ from each other, and therefore, an error is brought about in calculating the film thickness. Hence, by only including the insulating material 26 in the film thickness measuring region 14a as in the film thickness measuring region 14a of FIG. 13B, that is, by constituting inside of the region by a single material, the errors of the calibration data and data of measuring the film thickness can be restrained and the film thickness can be measured further accurately. Here, although an explanation has been given of the film thickness measuring region 14a, the same goes with the reference region 15a.

Meanwhile, when an electron beam is irradiated to a sample, a reflected electron is also generated other than the secondary electron. Although an explanation has been given of a method of measuring the film thickness by using the secondary electron, the film thickness cam also be measured by using the reflected electron in place of the secondary electron.

Figure 17:
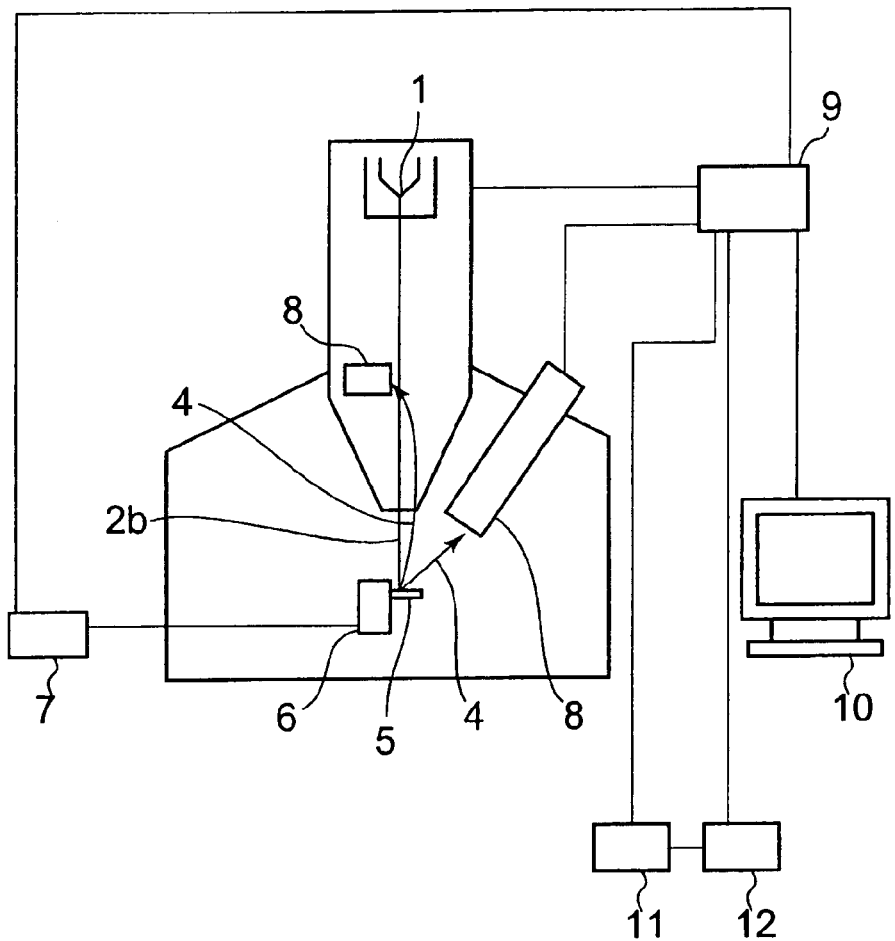
FIG. 17 is an outline view of a thin film sample measuring apparatus showing an embodiment of the invention.

The secondary electron detector normally collects the secondary electron by applying an attracting voltage in order to detect the secondary electron. At this occasion, the secondary electron is detected more than the reflected electron, and therefore, an amount of detecting the secondary electron becomes dominant. On the other hand, depending on an arrangement of the secondary electron detector, when the attracting voltage is not applied, there is a case in which an amount of detecting the reflected electron becomes dominant, and the secondary electron detector can also be used as a reflected electron detector. For example, FIG. 17 is an outline view of a thin film sample measuring apparatus showing an embodiment of the invention, and the secondary electron detector 8 is attached also at inside of a sample chamber and inside of the electron beam optical system. The reflected electron can be detected by adjusting an angle of incidence of the electron beam 2b to the sample or the attracting voltage of the secondary electron detector 8. Further, the reflected electron can be detected also by using a reflected electron detector using a semiconductor.

Figure 18:
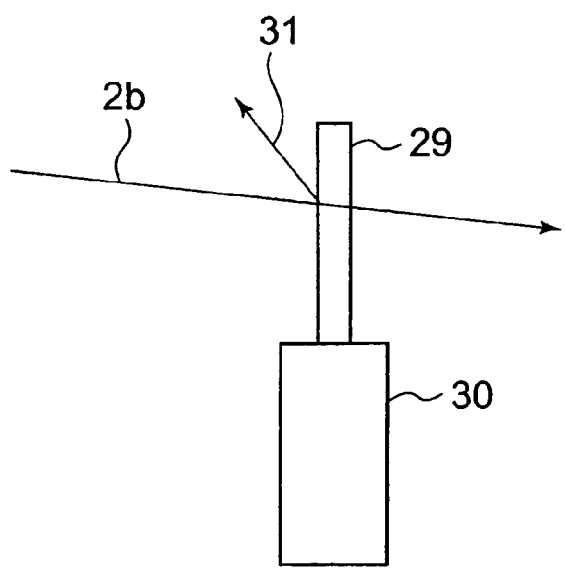
FIG. 18 is a schematic view of a sample showing an embodiment of the invention.
Figure 19:
FIG. 19 is a diagram of a relationship between a film thickness and a reflected electron amount showing an embodiment of the invention.
Figure 20:
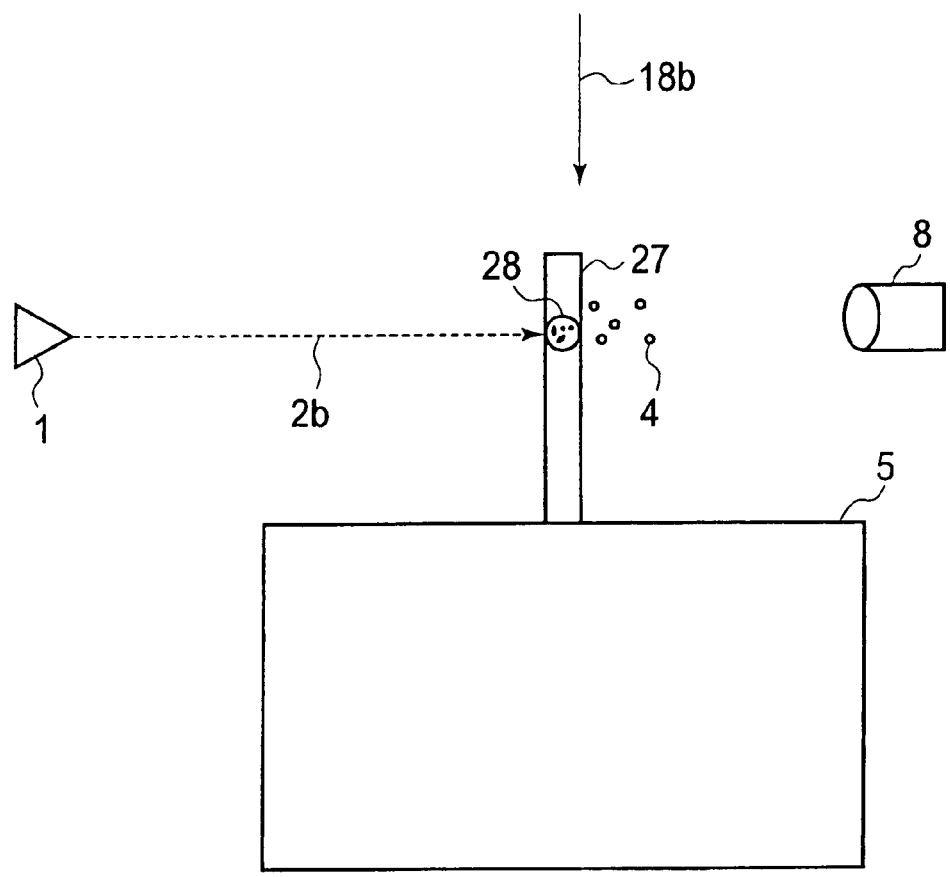
FIG. 20 is a sectional view of a sample showing a film thickness measuring method of a background art.

FIG. 18 shows the TEM sample 29 fixed to the TEM sample holder 30. When a film thickness of the TEM sample 29 is measured, a portion on which the transmitted electron beam 2b impinges is not present on a back side of the TEM sample 29. In this case, the film thickness can be measured by detecting not the secondary electron but the reflected electron 31. FIG. 19 shows a relationship between a film thickness and a reflected electron amount. The smaller the film thickness the smaller the reflected electron amount. According to the relationship, the reflected electron is reduced linearly relative to a reduction in the film thickness, and therefore, the film can further accurately be measured.

Further, according to the method of measuring the film thickness by using the secondary electron, when the sample is machined by using a focused ion beam, an Ar ion beam or the like, a secondary electron in accordance with machining is generated, and therefore, it is difficult to measure the film thickness. However, the secondary electron detecting efficiency of the reflected electron detector is low, and therefore, the film thickness can also be measured by detecting the reflected electron by irradiating the electron beam to the sample while machining the sample by using the focused ion beam, the Ar ion beam or the like. In this case, machining is not interrupted for measuring the film thickness, and therefore, an operational efficiency can be promoted.

Further, by using the reflected electron, even when the portion on which the electron beam 2b impinges is not present on the back side of the TEM sample 29 as in FIG. 18, it is not necessary to detect the secondary electron by the transmitted electron beam 2b, and therefore, the film thickness can be measured.

Further, although an explanation has been given of methods of separately utilizing the secondary electron and the reflected electron, the film thickness can also be measured by combining the secondary electron and the reflected electron.

According to the method and the apparatus of measuring the thin film sample and the method and the apparatus of fabricating the thin film sample, it can be provided that even when the current amount of the irradiated charged particle beam is varied, the film thickness is measured accurately, in a short period of time and easily. Further, by calculating the film thickness by using the calculated value uniquely determined by the film thickness of the film thickness measuring region without depending on the current amount of the irradiated charged particle beam, even when a plurality of samples are measured for a long period of time, the film thickness can accurately be measured without being effected with the influence of the variation in the current amount of the irradiated charged particle beam.

The invention claimed is:

1. A method of measuring a thin film sample characterized in including:

a step of detecting a charged particle generated by irradiating a charged particle beam to a region including a film thickness measuring region and a reference region of a standard thin film sample;

a step of calculating a calculated value of the standard thin film sample constituted by an amount of the charged particle detected at the film thickness measuring region and an amount of the charged particle detected at the reference region;

a step of forming a calibration data showing a relationship between the calculated value and the film thickness of the standard thin film sample;

a step of detecting a charged particle generated by irradiating a charged particle beam to a region including a film thickness measuring region and a reference region of a desired thin film sample;

a step of calculating a calculated value of the thin film sample constituted by an amount of the charged particle detected at the film thickness measuring region and an amount of the charged particle detected at the reference region; and a step of calculating the film thickness of the film thickness measuring region of the thin film sample from the calibration data and the calculated value of the thin film sample.

2. A method of measuring a thin film sample characterized in including:

a step of detecting a charged particle generated by irradiating a charged particle beam to a region including a film thickness measuring region and a reference region of a standard thin film sample;

a step of displaying an image of the charged particle on a display member by converting the detected charged particle into a luminance signal;

a step of designating the film thickness measuring region and the reference region from the displayed image of the charged particle;

a step of calculating a calculated value of the standard thin film sample constituted by a luminance of the film thickness measuring region and a luminance of the reference region;

a step of forming a calibration data showing a relationship between the calculated value and the film thickness of the standard thin film sample;

a step of detecting a charged particle generated by irradiating a charged particle beam to a region including a film thickness measuring region and a reference region of a desired thin film sample;

a step of displaying an image of the charged particle on a display member by converting a detected charged particle into a luminance signal;

a step of designating the film thickness measuring region and the reference region from a displayed image of the charged particle;

a step of calculating a calculated value of the thin film sample constituted by a luminance of the film thickness measuring region and a luminance of the reference region; and a step of calculating the film thickness of the film thickness measuring region of the thin film sample from the calibration data and the calculated value of the thin film sample.

3. The method of measuring a thin film sample according to claim 1, characterized in that the calculated values of the standard thin film sample and the thin film sample constituted by the amount of the charged particle detected at the film thickness measuring region and the amount of the charged particle detected at the reference region is a ratio of the amount of the charged particle detected at the film thickness measuring region to the amount of the charged particle detected at the reference region.

4. The method of measuring a thin film sample according to claim 2, characterized in that the calculated value of the standard thin film sample and the thin film sample constituted by the luminance of the thin film measuring region and the luminance of the reference region the is a ratio of the luminance of the film thickness measuring region to the luminance of the reference region.

5. The method of measuring a thin film sample according to claim 1, characterized in that the calculated value of the thin film sample is calculated by using an average value of the amounts of the charged particles at inside of the film thickness measuring region and an average value of the amounts of the charged particles at inside of the reference region, or an average value of the luminances at the film thickness measuring region and an average value of the luminances at the reference region.

6. The method of measuring a thin film sample according to claim 1, characterized in that an average value is calculated from the amounts of the charged particles or the luminances of a plurality of the reference regions and the calculated value of the thin film sample is calculated by using the average value.

7. The method of measuring a thin film sample according to claim 1, characterized in that an average value is calculated from the amounts of the charged particles or the luminances of a plurality of the film thickness measuring regions and the calculated value of the thin film sample is calculated by using the average value.

8. The method of measuring a thin film sample according to claim 1, characterized in that the film thicknesses of a plurality of the film thickness measuring regions are calculated.

9. The method of measuring a thin film sample according to claim 1, characterized in that inside of the film thickness measuring region and inside of the reference region are constituted by a single material.

10. The method of measuring a thin film sample according to claim 1, characterized in that a charged particle generated by irradiating the charged particle beam is constituted by a secondary electron.

11. The method of measuring a thin film sample according to claim 1, characterized in that a charged particle generated by irradiating the charged particle beam is constituted by a reflected electron.

12. The method of measuring a thin film sample according to claim 1, characterized in that a charged particle generated by irradiating the charged particle beam is added with a secondary electron and a reflected electron.

13. A method of fabricating a thin film sample characterized in including:

a step of scanning to irradiate a focused ion beam to a one side sample surface at a vicinity of a thin-filmed region of a desired sample to etch;

a step of scanning to irradiate a focused ion beam to an opposed side sample surface to the one side sample surface by interposing the thin-filmed region to etch;

a step of forming the thin-filmed region into a thin film by scanning to irradiate the focused ion beam to the vicinity of the thin-filmed region to etch;

a step of calculating a film thickness of the thin-filmed region to form into thin film by the method of measuring a thin film sample according to claim 1; and a step of etching the thin-filmed region until the calculated film thickness reaches a desired film thickness to form into the thin film.

14. A method of fabricating a thin film sample characterized in including:

a step of forming a calibration data showing a relationship between an amount of irradiating a focused ion beam and a film thickness of etching a standard thin film sample by scanning to irradiate the focused ion beam to a surface of the standard thin film sample to etch;

a step of scanning to irradiate a focused ion beam to a one side sample surface at a vicinity of a thin-filmed region of a desired sample to etch;

a step of scanning to irradiate a focused ion beam to a sample surface on a side opposed to the one side sample surface by interposing the thin-filmed region to etch;

a step of forming the thin-filmed region into a thin film by scanning to irradiate the focused ion beam to a vicinity of the thin-filmed region to etch;

a step of calculating a film thickness of the thin-filmed region to form into thin film by the method of measuring a thin film sample according to claim 1;

a step of calculating an amount of irradiating the focused ion beam necessary for making the calculated film thickness reach a desired film thickness from the calibration data; and a step of forming the thin-filmed region into the thin film by etching the thin-filmed region by the focused ion beam of the calculated irradiating amount.

15. An apparatus of measuring a thin film sample characterized in comprising:

a charged particle generating source for generating a charged particle;

a charged particle optical system for slenderly narrowing the charged particle into a charged particle beam to irradiate a surface of a sample while scanning the charged particle beam;

a charged particle detector for detecting a charged particle generated by irradiating the charged particle beam;

a display member for displaying an image of the charged particle by converting the charged particle detected by the charged particle detector into a luminance signal;

first calculating means for calculating a calculated value constituted by amounts of the charged particles or luminances of a plurality of regions; and second calculating means for calculating a film thickness of the film thickness measuring region from a calibration data constituting a function of a calculated value from a standard thin film sample constituted by amounts of the charged particles or luminances of a plurality of regions of the standard thin film sample and a film thickness of the standard thin film sample and the calculated value calculated by the first calculating means.

16. The apparatus of measuring a thin film sample according to claim 15, characterized in that a charged particle generated by irradiating the charged particle beam is constituted by a secondary electron.

17. The apparatus of measuring a thin film sample according to claim 15, characterized in that the charged particle generated by irradiating the charged particle beam is constituted by a reflected electron.

18. The apparatus of measuring a thin film sample according to claim 15, characterized in that the charged particle generated by irradiating the charged particle beam is added with a secondary electron and the reflected electron.

19. An apparatus of fabricating a thin film sample characterized in that the apparatus of measuring a thin film sample according to claim 15 further comprises an ion generating source for generating an ion; and an ion optical system for constituting an ion beam by slenderly narrowing the ion to irradiate a surface of a sample while scanning the ion beam.

20. The apparatus of fabricating a thin film sample according to claim 19, further comprising:

a third calculating mechanism for calculating an amount of irradiating the focused ion beam necessary for the film thickness calculated by the second calculating means to reach a desired film thickness.

* * * * *